United States Patent
Söll et al.

(10) Patent No.: US 6,492,131 B1
(45) Date of Patent: Dec. 10, 2002

(54) CLASS I-TYPE LYSYL-TRNA SYNTHETASE

(75) Inventors: Dieter Söll, Hamden, CT (US); Michael Ibba, Copenhagen (DK)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/508,370

(22) PCT Filed: Sep. 9, 1998

(86) PCT No.: PCT/US98/18968

§ 371 (c)(1), (2), (4) Date: Mar. 10, 2000

(87) PCT Pub. No.: WO99/13057

PCT Pub. Date: Mar. 18, 1999

Related U.S. Application Data

(60) Provisional application No. 60/058,420, filed on Sep. 10, 1997.

(51) Int. Cl.[7] .................................................. C12Q 1/48
(52) U.S. Cl. .......................................... 435/15; 435/183
(58) Field of Search ............................. 435/183, 6, 15; 536/23.1, 23.2

(56) References Cited

FOREIGN PATENT DOCUMENTS

WO      WO 98/58943     * 12/1998

OTHER PUBLICATIONS

Bult et al. Complete Genome Sequence of the Methanogenic Archaeon, *Methanococcus jannaschii*. Science (Aug. 1996) 273:1058–1073.*

GenBank Accession No. C64367 (Sep. 13, 1996).*

Soll et al. Context–dependent anticodon recognition by class I lysyl–tRNA synthetases. Proc Natl Acad Sci U S A Dec. 19, 2000; 97(26): 14224–8.*

Agou, F., et al., Biochemistry 1996, 35:15322–15331.

Chen, J., et al., J. Bacteriology 1994, 176:2699–2705.

Ibba, M., et al., Proc. Natl. Acad. Sci. USA 1997, 94:14383–14388.

Ibba, M., et al., TIBS 1997, 22: 39–42.

Ibba, M., et al., Proc. Natl. Acad. Sci. USA 1999, 96:418–423.

Ibba, M., et al., Science 1997, 278:1119–1122.

Schimmel, P., and Soll, D., Proc. Natl. Acad. Sci. USA 1997, 94: 10007–10009.

Tumbula, D., et al., Genetics 1999, 152:1269–1276.

* cited by examiner

*Primary Examiner*—Ponnathapu Achutamurthy
*Assistant Examiner*—Kathleen Kerr
(74) *Attorney, Agent, or Firm*—Mary M. Krinsky

(57) ABSTRACT

A protein with canonical lysyl-tRNA synthetase activity was purified from *Methanococcus maripaludis*, cloned, and sequenced. The predicted amino acid sequence of the enzyme indicated a novel class I polypeptide structurally unrelated to class II lysyl-tRNA synthetase reported in eubacteria, eukaryotes, and the Crenarchaeote *Sulfobus solfataricus*. A similar class I polypeptide was isolated from *Borrelia burgdorferi*, the causative agent of Lyme disease, and an open reading frame encoding a class I-type lysyl-tRNA synthetase was identified in the genome of *Treponema pallidum*, the causative agent of syphilis. The *B. burdorferi* gene encoding tRNALysl was cloned and used to make tRNA in vitro. The fundamental difference between pathogen and host in an essential enzyme suggests that class I-type lysyl-tRNA synthetase provides a target for the development of medical and veterinary therapeutics and diagnostics for Borrelia and other microorganism infections.

10 Claims, 3 Drawing Sheets

Figure 2

SEQUENCE LISTING

<160> NUMBER OF SEQ ID NOS: 16

<210> SEQ ID NO 1
<211> LENGTH: 494
<212> TYPE: PRT
<213> ORGANISM: Pyrococcus furiosus -continued

```
<220> FEATURE:
<221> NAME/KEY: lysyl t-RNA synthetase

<400> SEQUENCE: 1
```

Met Val His Trp Ala Asp Tyr Met Ala Glu Lys Ile Ile Lys Glu
                  5                  10                  15

Arg Gly Glu Lys Glu Glu Tyr Val Val Glu Ser Gly Ile Thr Pro
                 20                  25                  30

Ser Gly Tyr Val His Val Gly Asn Phe Arg Glu Leu Phe Thr Ala
                 35                  40                  45

Tyr Ile Val Gly His Ala Leu Arg Asp Arg Gly Tyr Asn Val Arg
                 50                  55                  60

His Ile His Met Trp Asp Asp Tyr Asp Arg Phe Arg Lys Val Pro
                 65                  70                  75

Lys Asn Val Pro Gln Glu Trp Glu Glu Tyr Leu Gly Met Pro Val
                 80                  85                  90

Ser Glu Val Pro Asp Pro Trp Gly Cys His Asp Ser Tyr Ala Glu
                 95                 100                 105

His Phe Met Gly Leu Phe Glu Glu Val Ala Lys Leu Glu Met
                110                 115                 120

Asp Val Glu Phe Leu Arg Ala Ser Glu Leu Tyr Lys Lys Gly Glu
                125                 130                 135

Tyr Ala Glu Glu Ile Arg Lys Ala Phe Glu Ala Lys Gly Lys Ile
                140                 145                 150

Met Ala Ile Leu Asn Lys Tyr Arg Glu Val Ala Lys Gln Pro Pro
                155                 160                 165

Leu Pro Glu Asn Trp Trp Pro Ala Met Val Tyr Cys Pro Glu His
                170                 175                 180

Arg Lys Glu Ser Glu Ile Ile Asp Trp Asp Gly Glu Trp Gly Val
                185                 190                 195

Lys Tyr Arg Cys Pro Glu Gly His Glu Gly Trp Thr Asp Ile Arg
                200                 205                 210

Asp Gly Asn Val Lys Leu Arg Trp Arg Val Asp Trp Pro Met Arg
                215                 220                 225

Trp Ala His Phe Gly Val Asp Phe Glu Pro Ala Gly Lys Asp His
                230                 235                 240

Leu Ala Ala Gly Ser Ser Tyr Asp Thr Gly Lys Glu Ile Ile Arg
                245                 250                 255

Glu Val Tyr Gly Lys Glu Ala Pro Leu Thr Leu Met Tyr Glu Phe
                260                 265                 270

Val Gly Ile Lys Gly Gln Lys Gly Lys Met Ser Gly Ser Lys Gly
                275                 280                 285

Asn Val Ile Leu Leu Ser Asp Leu Tyr Glu Val Leu Glu Pro Gly
                290                 295                 300

Leu Val Arg Phe Ile Tyr Ala Lys His Arg Pro Asn Lys Glu Ile
                305                 310                 315

Arg Ile Asp Leu Gly Leu Gly Leu Leu Asn Leu Tyr Asp Glu Phe
                320                 325                 330

Asp Arg Val Glu Arg Ile Tyr Phe Gly Ile Glu Lys Gly Lys Gly
                335                 340                 345

Asp Glu Glu Glu Leu Lys Arg Thr Tyr Glu Leu Ser Val Pro Lys
                350                 355                 360

Lys Pro Lys Arg Leu Val Ala Gln Ala Pro Phe Arg Phe Leu Ala
                365                 370                 375

```
Val Leu Val Gln Leu Pro His Leu Ser Ile Glu Asp Ile Ile Phe
            380                 385                 390

Thr Leu Val Lys Gln Gly His Val Pro Glu Asn Leu Thr Gln Glu
            395                 400                 405

Asp Ile Asp Arg Ile Lys Leu Arg Ile Lys Leu Ala Lys Asn Trp
            410                 415                 420

Val Glu Lys Tyr Ala Pro Glu Val Lys Phe Lys Ile Leu Ser
            425                 430                 435

Val Pro Gly Val Ser Glu Val Asp Pro Thr Ile Arg Glu Ala Met
            440                 445                 450

Leu Glu Val Ala Glu Trp Leu Glu Ser His Glu Asp Phe Ala Val
            455                 460                 465

Asp Glu Leu Asn Asn Ile Leu Phe Glu Val Ala Lys Lys Arg Asn
            470                 475                 480

Ile Pro Ser Lys Val Trp Phe Ser His Cys Thr Asn Tyr Ser
            485                 490

<210> SEQ ID NO 2
<211> LENGTH: 523
<212> TYPE: PRT
<213> ORGANISM: Pyrococcus horikoshii
<220> FEATURE:
<221> NAME/KEY: lysyl t-RNA synthetase

<400> SEQUENCE: 2

Met Val His Trp Ala Asp Tyr Ile Ala Asp Lys Ile Ile Arg Glu
              5                  10                  15

Arg Gly Glu Lys Glu Lys Tyr Val Val Glu Ser Gly Ile Thr Pro
             20                  25                  30

Ser Gly Tyr Val His Val Gly Asn Phe Arg Glu Leu Phe Thr Ala
             35                  40                  45

Tyr Ile Val Gly His Ala Leu Arg Asp Lys Gly Tyr Glu Val Arg
             50                  55                  60

His Ile His Met Trp Asp Asp Tyr Asp Arg Phe Arg Lys Val Pro
             65                  70                  75

Arg Asn Val Pro Gln Glu Trp Lys Asp Tyr Leu Gly Met Pro Ile
             80                  85                  90

Ser Glu Val Pro Asp Pro Trp Gly Cys His Glu Ser Tyr Ala Glu
             95                 100                 105

His Phe Met Arg Lys Phe Glu Glu Val Glu Lys Leu Gly Ile
            110                 115                 120

Glu Val Asp Phe Leu Tyr Ala Ser Glu Leu Tyr Lys Arg Gly Glu
            125                 130                 135

Tyr Ser Glu Glu Ile Arg Leu Ala Phe Glu Lys Arg Asp Lys Ile
            140                 145                 150

Met Glu Ile Leu Asn Lys Tyr Arg Glu Ile Ala Lys Gln Pro Pro
            155                 160                 165

Leu Pro Glu Asn Trp Trp Pro Ala Met Val Tyr Cys Pro Glu His
            170                 175                 180

Arg Arg Glu Ala Glu Ile Ile Glu Trp Asp Gly Gly Trp Lys Val
            185                 190                 195

Lys Tyr Lys Cys Pro Glu Gly His Glu Gly Trp Val Asp Ile Arg
            200                 205                 210

Ser Gly Asn Val Lys Leu Arg Trp Arg Val Asp Trp Pro Met Arg
            215                 220                 225
```

-continued

```
Trp Ser His Phe Gly Val Asp Phe Glu Pro Ala Gly Lys Asp His
            230                 235                 240

Leu Val Ala Gly Ser Ser Tyr Asp Thr Gly Lys Glu Ile Ile Lys
            245                 250                 255

Glu Val Tyr Gly Lys Glu Ala Pro Leu Ser Leu Met Tyr Glu Phe
            260                 265                 270

Val Gly Ile Lys Gly Gln Lys Gly Lys Met Ser Gly Ser Lys Gly
            275                 280                 285

Asn Val Ile Leu Leu Ser Asp Leu Tyr Glu Val Leu Glu Pro Gly
            290                 295                 300

Leu Val Arg Phe Ile Tyr Ala Arg His Arg Pro Asn Lys Glu Ile
            305                 310                 315

Lys Ile Asp Leu Gly Leu Gly Ile Leu Asn Leu Tyr Asp Glu Phe
            320                 325                 330

Asp Lys Val Glu Arg Ile Tyr Phe Gly Val Glu Gly Gly Lys Gly
            335                 340                 345

Asp Asp Glu Glu Leu Arg Arg Thr Tyr Glu Leu Ser Met Pro Lys
            350                 355                 360

Lys Pro Glu Arg Leu Val Ala Gln Ala Pro Phe Arg Phe Leu Ala
            365                 370                 375

Val Leu Val Gln Leu Pro His Leu Thr Glu Glu Asp Ile Ile Asn
            380                 385                 390

Val Leu Ile Lys Gln Gly His Ile Pro Arg Asp Leu Ser Lys Glu
            395                 400                 405

Asp Val Glu Arg Val Lys Leu Arg Ile Asn Leu Ala Arg Asn Trp
            410                 415                 420

Val Lys Lys Tyr Ala Pro Glu Asp Val Lys Phe Ser Ile Leu Glu
            425                 430                 435

Lys Pro Pro Glu Val Glu Val Ser Glu Asp Val Arg Glu Ala Met
            440                 445                 450

Asn Glu Val Ala Glu Trp Leu Glu Asn His Glu Glu Phe Ser Val
            455                 460                 465

Glu Glu Phe Asn Asn Ile Leu Phe Glu Val Ala Lys Arg Arg Gly
            470                 475                 480

Ile Ser Ser Arg Glu Trp Phe Ser Thr Leu Tyr Arg Leu Phe Ile
            485                 490                 495

Gly Lys Glu Arg Gly Pro Arg Leu Ala Ser Phe Leu Ala Ser Leu
            500                 505                 510

Asp Arg Ser Phe Val Ile Lys Arg Leu Arg Leu Glu Gly
            515                 520

<210> SEQ ID NO 3
<211> LENGTH: 521
<212> TYPE: PRT
<213> ORGANISM: Borrelia burgdorferi
<220> FEATURE:
<221> NAME/KEY: lysyl t-RNA synthetase
<223> OTHER INFORMATION: construct expressed in Example 3

<400> SEQUENCE: 3

Met Lys Thr Ala His Trp Ala Asp Phe Tyr Ala Glu Lys Ile Lys
              5                  10                  15

Lys Glu Lys Gly Pro Lys Asn Leu Tyr Thr Val Ala Ser Gly Ile
             20                  25                  30

Thr Pro Ser Gly Thr Val His Ile Gly Asn Phe Arg Glu Val Ile
```

```
                        35                  40                  45
Ser Val Asp Leu Val Ala Arg Ala Leu Arg Asp Ser Gly Ser Lys
                50                  55                  60
Val Arg Phe Ile Tyr Ser Trp Asp Asn Tyr Asp Val Phe Arg Lys
                65                  70                  75
Val Pro Lys Asn Met Pro Glu Gln Glu Leu Leu Thr Thr Tyr Leu
                80                  85                  90
Arg Gln Ala Ile Thr Arg Val Pro Asp Thr Arg Ser His Lys Thr
                95                 100                 105
Ser Tyr Ala Arg Ala Asn Glu Ile Glu Phe Glu Lys Tyr Leu Pro
               110                 115                 120
Val Val Gly Ile Asn Pro Glu Phe Ile Asp Gln Ser Lys Gln Tyr
               125                 130                 135
Thr Ser Asn Ala Tyr Ala Ser Gln Ile Lys Phe Ala Leu Asp His
               140                 145                 150
Lys Lys Glu Leu Ser Glu Ala Leu Asn Glu Tyr Arg Thr Ser Lys
               155                 160                 165
Leu Glu Glu Asn Trp Tyr Pro Ile Ser Val Phe Cys Thr Lys Cys
               170                 175                 180
Asn Arg Asp Thr Thr Thr Val Asn Asn Tyr Asp Asn His Tyr Ser
               185                 190                 195
Val Glu Tyr Ser Cys Glu Cys Gly Asn Gln Glu Ser Leu Asp Ile
               200                 205                 210
Arg Thr Thr Trp Ala Ile Lys Leu Pro Trp Arg Ile Asp Trp Pro
               215                 220                 225
Met Arg Trp Lys Tyr Glu Lys Val Asp Phe Glu Pro Ala Gly Lys
               230                 235                 240
Asp His His Ser Ser Gly Gly Ser Phe Asp Thr Ser Lys Asn Ile
               245                 250                 255
Val Lys Ile Phe Gln Gly Ser Pro Pro Val Thr Phe Gln Tyr Asp
               260                 265                 270
Phe Ile Ser Ile Lys Gly Arg Gly Gly Lys Ile Ser Ser Ser Ser
               275                 280                 285
Gly Asp Val Ile Ser Leu Lys Asp Val Leu Glu Val Tyr Thr Pro
               290                 295                 300
Glu Val Thr Arg Phe Leu Phe Ala Ala Thr Lys Pro Asn Thr Glu
               305                 310                 315
Phe Ser Ile Ser Phe Asp Leu Asp Val Ile Lys Ile Tyr Glu Asp
               320                 325                 330
Tyr Asp Lys Phe Glu Arg Ile Tyr Tyr Gly Val Glu Asp Val Lys
               335                 340                 345
Glu Glu Lys Lys Arg Ala Phe Lys Arg Ile Tyr Glu Leu Ser Gln
               350                 355                 360
Pro Tyr Met Pro Ser Lys Arg Ile Pro Tyr Gln Val Gly Phe Arg
               365                 370                 375
His Leu Ser Val Ile Ser Gln Ile Phe Glu Asn Asn Ile Asn Lys
               380                 385                 390
Ile Leu Asn Tyr Leu Lys Asn Val Gln Glu Asp Gln Lys Asp Lys
               395                 400                 405
Leu Ile Asn Lys Ile Asn Cys Ala Ile Asn Trp Ile Arg Asp Phe
               410                 415                 420
Ala Pro Glu Asp Phe Lys Phe Ser Leu Arg Ser Lys Phe Asp Asn
               425                 430                 435
```

```
Met Glu Ile Leu Glu Glu Asn Ser Lys Lys Ala Ile Asn Glu Leu
                440                 445                 450

Leu Asp Phe Leu Lys Lys Asn Phe Glu Val Ala Thr Glu Gln Asp
                455                 460                 465

Ile Gln Asn Glu Ile Tyr Lys Ile Ser Arg Glu Asn Asn Ile Glu
                470                 475                 480

Pro Ala Leu Phe Phe Lys Gln Ile Tyr Lys Ile Leu Ile Asp Lys
                485                 490                 495

Glu Lys Gly Pro Lys Leu Ala Gly Phe Ile Lys Ile Ile Gly Ile
                500                 505                 510

Asp Arg Phe Glu Lys Ile Thr Ser Lys Tyr Val
                515                 520

<210> SEQ ID NO 4
<211> LENGTH: 528
<212> TYPE: PRT
<213> ORGANISM: Treponema pallidum
<220> FEATURE:
<221> NAME/KEY: lysyl t-RNA synthetase

<400> SEQUENCE: 4

Met Ser Ile Cys Glu Lys Ser Leu His Trp Ala Asp Lys Val Ala
                  5                  10                  15

His Lys Ile Ile Lys Glu Arg Ala Asp Cys Asp Gln Tyr Thr Cys
                 20                  25                  30

Ala Ser Gly Ile Thr Pro Ser Gly Thr Val His Ile Gly Asn Phe
                 35                  40                  45

Arg Glu Ile Ile Ser Val Asp Leu Val Val Arg Ala Leu Arg Asp
                 50                  55                  60

Gln Gly Lys Ser Val Arg Phe Val His Ser Trp Asp Asp Tyr Asp
                 65                  70                  75

Val Phe Arg Arg Ile Pro Asp Asn Val Pro Ala Gln Asp Glu Leu
                 80                  85                  90

Lys Gln Tyr Ile Arg Met Pro Ile Thr Ser Val Pro Asp Pro Phe
                 95                 100                 105

Gln Gln Glu Asp Ser Tyr Ala Arg His Glu Arg Glu Ile Glu
                110                 115                 120

Ser Ala Leu Pro Glu Val Gly Ile Tyr Pro Glu Tyr Val Tyr Gln
                125                 130                 135

Ser Lys Gln Tyr Gln Ala Gly Val Tyr Ala Gln Glu Ile Lys Ile
                140                 145                 150

Ala Leu Asp Asn Arg His Arg Ile Gln Ala Ile Leu Asn Glu Tyr
                155                 160                 165

Arg Asp Glu Gln His Lys Ile Ser Gly Thr Tyr Trp Pro Val Ser
                170                 175                 180

Val Phe Cys Thr Ala Cys His Lys Asp Cys Thr Thr Val Asp Ala
                185                 190                 195

Trp Asp Ser His Trp Cys Leu Gln Tyr His Cys Glu Cys Gly His
                200                 205                 210

Gly Glu Gln Val Asp Leu Arg Gln Thr Ser Ala Val Lys Leu Ser
                215                 220                 225

Trp Arg Val Asp Trp Ala Met Arg Trp Ser Lys Glu His Val Val
                230                 235                 240

Phe Glu Pro Ala Gly Lys Asp His Ser Gln Gly Gly Ser Phe
                245                 250                 255
```

```
Asp Thr Ala Arg Leu Ile Ser Asp His Ile Tyr His Trp Pro Ala
            260                 265                 270
Pro Val Ser Phe Arg Tyr Asp Phe Ile Gly Leu Lys Gly Met Pro
            275                 280                 285
Gly Lys Met Ser Ser Ala Gly Lys Val Val Gly Leu Arg Asp
            290                 295                 300
Val Leu Glu Val Tyr Gln Pro Glu Val Leu Arg Tyr Leu Phe Val
            305                 310                 315
Ser Thr Arg Pro Asn Thr Glu Phe Ser Ile Ser Phe Asp Leu Asp
            320                 325                 330
Val Leu Lys Ile Tyr Glu Asp Tyr Asp Lys Ser Glu Arg Val Ala
            335                 340                 345
Trp Gly Ile His Ala Ala Lys Ser Glu His Glu Phe Met Arg His
            350                 355                 360
Lys Arg Ile Tyr Glu Leu Ser Gln Val Arg Gly Met Pro Pro Cys
            365                 370                 375
Ile Ser Tyr Gln Val Pro Phe Arg His Val Cys Asn Ile Leu Gln
            380                 385                 390
Ile Asn Ser Gly Asp Ile Ser Ala Val Leu Ala Phe Phe Ser Asp
            395                 400                 405
Ile His Lys Asp Gln Ile Glu Arg Phe Val Arg Arg Cys Gln Cys
            410                 415                 420
Ala Trp Asn Trp Ile Arg Asp Ala Gly Ala Pro Asp Asp Phe Lys
            425                 430                 435
Phe Thr Leu Lys Glu Asp Gly Val Arg Val Pro Leu Ser Ala Glu
            440                 445                 450
Ile Thr Glu Ala Leu Arg Leu Ile Arg Asp Thr Leu Val Pro Arg
            455                 460                 465
Thr Asp Val Leu Ser Glu Lys Glu Leu Ser Ala Glu Leu Tyr Ala
            470                 475                 480
Val Ala Arg Gln Ile Pro Val Gly Ser Lys Glu Leu Phe Thr Ala
            485                 490                 495
Leu Tyr Gln Val Leu Ile Gly Lys Asn Gln Gly Pro Arg Leu Ala
            500                 505                 510
Gly Phe Met Lys Val Ile Gly Thr Gln Arg Leu His Arg Met Leu
            515                 520                 525
Ser Val Tyr

<210> SEQ ID NO 5
<211> LENGTH: 534
<212> TYPE: PRT
<213> ORGANISM: Methanococcus jannaschii
<220> FEATURE:
<221> NAME/KEY: lysyl t-RNA synthetase

<400> SEQUENCE: 5

Leu Arg Glu Ile Met His Trp Ala Asp Val Ile Ala Glu Lys Leu
            5                   10                  15
Ile Glu Glu Arg Lys Ala Asp Lys Tyr Ile Val Ala Ser Gly Ile
            20                  25                  30
Thr Pro Ser Gly His Ile His Val Gly Asn Ala Arg Glu Thr Leu
            35                  40                  45
Thr Ala Asp Ala Ile Tyr Lys Gly Leu Ile Asn Lys Gly Val Glu
            50                  55                  60
```

-continued

```
Ala Glu Leu Ile Phe Ile Ala Asp Thr Tyr Asp Pro Leu Arg Lys
             65                  70                  75

Leu Tyr Pro Phe Leu Pro Lys Glu Phe Glu Gln Tyr Ile Gly Met
             80                  85                  90

Pro Leu Ser Glu Ile Pro Cys Pro Glu Gly Cys Cys Glu Ser Tyr
             95                 100                 105

Ala Glu His Phe Leu Arg Pro Tyr Leu Glu Ser Leu Asp Asp Leu
            110                 115                 120

Gly Val Glu Leu Thr Thr Tyr Arg Ala Asp Glu Asn Tyr Lys Lys
            125                 130                 135

Gly Leu Tyr Asp Glu Lys Ile Lys Ile Ala Leu Asp Asn Arg Glu
            140                 145                 150

Lys Ile Met Glu Ile Leu Asn Lys Phe Arg Ala Asn Pro Leu Pro
            155                 160                 165

Asp Asp Trp Trp Pro Ile Asn Ile Val Cys Glu Asn Cys Gly Lys
            170                 175                 180

Leu Lys Thr Lys Val Ile Lys Tyr Asp Ser Glu Lys Glu Glu Ile
            185                 190                 195

Thr Tyr Arg Cys Glu Ile Cys Gly Phe Glu Asn Thr Val Lys Pro
            200                 205                 210

Tyr Lys Gly Arg Ala Lys Leu Pro Trp Arg Val Asp Trp Pro Ala
            215                 220                 225

Arg Trp Ser Ile Phe Asn Val Thr Ile Glu Pro Met Gly Lys Asp
            230                 235                 240

His Ala Ala Ala Gly Gly Ser Tyr Asp Thr Gly Val Leu Ile Ala
            245                 250                 255

Lys Glu Ile Tyr Asn Tyr Ile Pro Pro Lys Val Val Tyr Glu
            260                 265                 270

Trp Ile Gln Leu Lys Val Gly Asp Lys Ala Ile Pro Met Ser Ser
            275                 280                 285

Ser Lys Gly Val Val Phe Ala Val Lys Asp Trp Thr Asn Ile Ala
            290                 295                 300

His Pro Glu Ile Leu Arg Phe Leu Leu Leu Arg Ser Lys Pro Thr
            305                 310                 315

Lys His Ile Asp Phe Asp Leu Lys Lys Ile Pro Asp Leu Val Asp
            320                 325                 330

Glu Tyr Asp Arg Leu Glu Asp Phe Tyr Phe Asn Asn Lys Asp Lys
            335                 340                 345

Asp Glu Leu Ser Glu Glu Glu Gln Lys Ile Arg Ile Tyr Glu
            350                 355                 360

Leu Ser Thr Pro Lys Ile Pro Glu Thr Lys Pro Phe Val Ile Pro
            365                 370                 375

Tyr Arg Phe Cys Ser Ile Ile Ala Gln Leu Thr Tyr Asp Glu Glu
            380                 385                 390

Lys Glu Asp Ile Asn Met Glu Arg Val Phe Glu Ile Leu Arg Arg
            395                 400                 405

Asn Asn Tyr Ser Ile Asp Asp Ile Asp Glu Phe Ser Met Lys Lys
            410                 415                 420

Leu Lys Asp Arg Leu Leu Met Ala Arg Asn Trp Ala Leu Lys Tyr
            425                 430                 435

Gly Glu Lys Leu Val Ile Ile Ser Glu Asp Glu Ala Lys Glu Ile
            440                 445                 450

Tyr Glu Lys Leu Lys Asp Lys Gln Lys Glu Trp Ile Lys Tyr Phe
```

```
                        455                 460                 465
Ala Glu Lys Leu Lys Thr Ala Glu Phe Asp Ala Leu Asn Leu His
                    470                 475                 480

Glu Leu Ile Tyr Gln Thr Ala Lys Glu Leu Gly Leu Asn Pro Arg
                485                 490                 495

Asp Ala Phe Gln Ala Ser Tyr Met Ile Leu Leu Gly Lys Lys Tyr
            500                 505                 510

Gly Pro Lys Leu Gly Ala Phe Leu Ala Thr Leu Gly Lys Asp Phe
        515                 520                 525

Val Ile Arg Arg Tyr Ser Leu Phe Glu
                    530
```

<210> SEQ ID NO 6
<211> LENGTH: 533
<212> TYPE: PRT
<213> ORGANISM: Methanococcus maripaludis
<220> FEATURE:
<221> NAME/KEY: lysyl t-RNA synthetase
<223> OTHER INFORMATION: construct expressed in Example 1

<400> SEQUENCE: 6

```
Met His Trp Ala Asp Ala Thr Ser Glu Lys Ile Met Lys Lys Arg
                  5                 10                  15

Asn Ala Glu Glu Tyr Val Val Ser Ser Gly Ile Thr Pro Ser Gly
                 20                  25                  30

His Ile His Ile Gly Asn Ala Arg Glu Thr Leu Thr Ala Asp Ala
                 35                  40                  45

Val Tyr Lys Gly Met Leu Lys Lys Gly Ala Glu Ala Lys Leu Ile
                 50                  55                  60

Phe Ile Ala Asp Asp Tyr Asp Pro Leu Arg Lys Leu Tyr Pro Phe
                 65                  70                  75

Leu Pro Lys Glu Phe Glu Lys Tyr Ile Gly Met Pro Leu Ser Glu
                 80                  85                  90

Ile Pro Cys Pro Gln Gly Cys Cys Lys Ser Tyr Ala Asp His Phe
                 95                 100                 105

Leu Met Pro Phe Leu Asn Ser Leu Glu Asp Leu Gly Val Glu Ile
                110                 115                 120

Thr Thr His Arg Ala Asn Glu Cys Tyr Lys Ala Gly Met Tyr Asn
                125                 130                 135

Glu Ala Ile Ile Thr Ala Leu Glu Asn Arg Leu Lys Ile Lys Glu
                140                 145                 150

Leu Leu Asp Ser Tyr Arg Lys Glu Pro Leu Ala Asp Asn Trp Tyr
                155                 160                 165

Pro Leu Asn Val Val Cys Glu Lys Cys Gly Lys Met His Glu Thr
                170                 175                 180

Lys Val Thr Ser Tyr Asn Ser Glu Asp Lys Thr Ile Thr Tyr Val
                185                 190                 195

Cys Lys Cys Gly Phe Glu Asn Thr Val Gln Pro Phe Asn Gly Ile
                200                 205                 210

Gly Lys Leu Pro Trp Arg Val Asp Trp Pro Ala Arg Trp Asn Ile
                215                 220                 225

Phe Gly Val Thr Ala Glu Pro Met Gly Lys Asp His Ala Ala Ser
                230                 235                 240

Gly Gly Ser Tyr Asp Thr Gly Ile Lys Ile Ala Arg Gln Ile Phe
                245                 250                 255
```

```
Asn Tyr Gln Ala Pro Glu Lys Met Val Tyr Glu Trp Ile Gln Leu
                260                 265                 270

Lys Ile Gly Asp Lys Ala Met Pro Met Ser Ser Ser Ser Gly Val
                275                 280                 285

Val Phe Ala Val Lys Asp Trp Thr Glu Ile Cys His Pro Glu Val
                290                 295                 300

Leu Arg Phe Leu Ile Leu Lys Gly Lys Pro Thr Lys His Ile Asp
                305                 310                 315

Phe Asp Leu Lys Ala Ile Ser Asn Leu Val Asp Asp Tyr Asp Glu
                320                 325                 330

Leu Glu Arg Lys Tyr Phe Glu Leu Ile Glu Lys Gln Lys Thr Glu
                335                 340                 345

Glu Leu Asn Asp Asn Glu Asn Glu Lys Ile Ser Leu Tyr Glu Leu
                350                 355                 360

Val Thr Pro Lys Ile Pro Glu Arg Leu Pro Leu Gln Val Ala Tyr
                365                 370                 375

Arg Phe Cys Ser Ile Ile Ala Gln Ile Ala Leu Asp Lys Glu Thr
                380                 385                 390

Gln Lys Ile Asp Met Glu Arg Val Phe Asp Ile Leu Gly Arg Asn
                395                 400                 405

Gly Tyr Asn Pro Ala Glu Phe Ser Glu Tyr Asp Lys Ser Arg Leu
                410                 415                 420

Glu Lys Arg Leu Tyr Met Ser Lys Lys Trp Ala Ser Asp Tyr Gly
                425                 430                 435

Glu Asn Leu Glu Ile Asn Asp Phe Glu Gln Ala Lys Glu Gln Tyr
                440                 445                 450

Glu Thr Leu Ser Glu Glu Gln Lys Ala Trp Leu Lys Ala Phe Ser
                455                 460                 465

Lys Glu Val Glu Asn Ile Glu Ile Asp Ala Asn Thr Ile His Glu
                470                 475                 480

Leu Met Tyr Glu Thr Ala Thr Lys Leu Asn Leu Ala Pro Lys Glu
                485                 490                 495

Ala Phe Val Ala Ser Tyr Lys Ile Leu Leu Gly Lys Asn Tyr Gly
                500                 505                 510

Pro Lys Leu Gly Ser Phe Leu Ala Ser Leu Lys Lys Glu Phe Val
                515                 520                 525

Ile Gly Arg Phe Asn Leu Thr Glu
                530

<210> SEQ ID NO 7
<211> LENGTH: 493
<212> TYPE: PRT
<213> ORGANISM: Archaeolglobus fulgidus
<220> FEATURE:
<221> NAME/KEY: lysyl t-RNA synthetase

<400> SEQUENCE: 7

Met His Trp Ala Asp Val Ile Ala Ala Asp Leu Leu Lys Arg Ser
                5                   10                  15

Asn Ser His Arg Ile Ala Thr Gly Ile Ser Pro Ser Gly His Ile
                20                  25                  30

His Leu Gly Asn Leu Arg Glu Met Val Thr Ala Asp Ala Ile Arg
                35                  40                  45

Arg Ala Leu Leu Asp Ala Gly Gly Glu Ala Lys Ile Val Tyr Ile
                50                  55                  60
```

-continued

```
Ala Asp Asp Phe Asp Pro Leu Arg Arg Tyr Pro Phe Leu Pro
             65                  70                  75

Glu Glu Tyr Glu Asn Tyr Val Gly Met Pro Leu Cys Lys Ile Pro
                 80                  85                  90

Asp Pro Glu Gly Cys His Asp Ser Tyr Ser Glu His Phe Leu Gln
                 95                 100                 105

Pro Phe Leu Glu Ser Leu Glu Ile Leu Gly Ile Pro Val Glu Val
                110                 115                 120

Arg Arg Ala Tyr Gln Met Tyr Ser Glu Gly Leu Tyr Glu Asn Asn
                125                 130                 135

Thr Arg Ile Ala Leu Lys Arg Arg Asp Glu Ile Ala Arg Ile Ile
                140                 145                 150

Ala Glu Val Thr Gly Arg Glu Leu Glu Glu Arg Trp Tyr Pro Phe
                155                 160                 165

Met Pro Leu Cys Glu Asn Cys Gly Arg Ile Asn Ser Thr Arg Val
                170                 175                 180

Thr Ser Phe Asp Glu Asn Trp Ile Tyr Tyr Glu Cys Asp Cys Gly
                185                 190                 195

His Ser Gly Arg Val Gly Tyr Val Gly Gly Lys Leu Thr Trp
                200                 205                 210

Arg Val Asp Trp Ala Ala Arg Trp Gln Ile Leu Ser Ile Thr Cys
                215                 220                 225

Glu Pro Phe Gly Lys Asp His Ala Ala Ala Gly Gly Ser Tyr Asp
                230                 235                 240

Thr Gly Val Arg Ile Ala Arg Glu Ile Phe Asp Tyr Glu Pro Pro
                245                 250                 255

Tyr Pro Val Pro Tyr Glu Trp Ile His Leu Lys Gly Lys Gly Ala
                260                 265                 270

Met Lys Ser Ser Lys Gly Ile Val Leu Pro Val Arg Glu Met Val
                275                 280                 285

Glu Val Ile Pro Pro Glu Ile Val Arg Tyr Ile Thr Ile Arg Val
                290                 295                 300

Lys Pro Glu Arg His Ile Glu Phe Asp Pro Gly Leu Gly Leu Leu
                305                 310                 315

Asp Leu Val Glu Glu Phe Glu Glu Lys Phe Lys Glu Lys Asp Arg
                320                 325                 330

Ser Val Glu Leu Ser Leu Val Gly Glu Val Val Tyr Ser Asp Val
                335                 340                 345

Pro Phe Arg His Leu Ile Val Val Gly Gln Ile Ala Asn Trp Asp
                350                 355                 360

Leu Glu Lys Ala Leu Glu Ile Ile Glu Arg Thr Gly Tyr Thr Val
                365                 370                 375

Asp Asp Val Thr Arg Arg Asp Val Glu Arg Arg Leu Lys Tyr Ala
                380                 385                 390

Arg Lys Trp Leu Glu Lys Tyr Ala Pro Asp Asn Ile Lys Phe Glu
                395                 400                 405

Ile Pro Glu Lys Val Thr Ala Glu Phe Ser Glu Glu Lys Lys
                410                 415                 420

Phe Leu Arg Ala Tyr Ala Glu Arg Leu Arg Ser Asp Met Lys Pro
                425                 430                 435

Glu Glu Ile His Thr Leu Val Tyr Asp Val Ser Lys Glu Val Gly
                440                 445                 450

Ile Lys Ser Ser Lys Ala Phe Gln Ala Ile Tyr Lys Ala Ile Leu
```

```
                          455                 460                 465
Gly Lys Thr Tyr Gly Pro Arg Val Gly Tyr Phe Ile Lys Ser Leu
                      470                 475                 480
Gly Val Glu Trp Val Arg Glu Arg Ile Lys Ala Ala Leu
                  485                 490

<210> SEQ ID NO 8
<211> LENGTH: 513
<212> TYPE: PRT
<213> ORGANISM: Methanobacterium thermoautotrophicum
<220> FEATURE:
<221> NAME/KEY: lysyl t-RNA synthetase

<400> SEQUENCE: 8

Leu Lys Glu Arg Asp Val Glu His Val Val Ala Ser Gly Thr
                  5                  10                  15
Ser Ile Ser Gly Ser Ile His Ile Gly Asn Ser Cys Asp Val Phe
                  20                  25                  30
Ile Ala Ser Ser Ile Ala Lys Ser Leu Lys Lys Asp Gly Phe Lys
                  35                  40                  45
Ser Arg Thr Val Trp Ile Ala Asp Asp His Asp Pro Leu Arg Lys
                  50                  55                  60
Val Pro Tyr Pro Leu Pro Glu Ser Tyr Glu Lys Tyr Leu Gly Val
                  65                  70                  75
Pro Tyr Ser Met Ile Pro Cys Pro Glu Gly Cys Cys Glu Ser Phe
                  80                  85                  90
Val Glu His Phe Gln Arg Pro Phe Leu Glu Ala Leu Glu Arg Phe
                  95                  100                 105
Arg Ile Gly Val Glu His Tyr Ser Gly Ala Arg Met Tyr Thr Glu
                  110                 115                 120
Gly Leu Tyr Asn Asp Tyr Ile Arg Thr Ser Leu Glu Arg Ala Pro
                  125                 130                 135
Glu Ile Arg Glu Ile Phe Asn Arg Phe Arg Asp Arg Pro Leu Arg
                  140                 145                 150
Asp Asp Trp Leu Pro Tyr Asn Pro Ile Cys Glu Lys Cys Gly Arg
                  155                 160                 165
Val Asn Thr Thr Glu Ala Tyr Asp Phe Ser Gly Asp Thr Val Arg
                  170                 175                 180
Tyr Arg Cys Glu Cys Gly Phe Asp Gly Glu Met Asp Ile Lys Ser
                  185                 190                 195
Gly Leu Gly Lys Leu Thr Trp Arg Val Glu Trp Ala Ala Arg Trp
                  200                 205                 210
Lys Ile Leu Gly Val Thr Cys Glu Pro Phe Gly Lys Asp His Ala
                  215                 220                 225
Ala Ser Gly Gly Ser Tyr Asp Val Ser Ser Ile Ile Ser Glu Glu
                  230                 235                 240
Ile Phe Asp Tyr Pro Ala Pro Tyr Pro Val Pro Tyr Glu Trp Ile
                  245                 250                 255
Thr Leu Arg Gly Glu Ala Met Ser Lys Ser Arg Gly Val Phe Phe
                  260                 265                 270
Thr Pro Gly Gln Trp Leu Glu Ile Gly Pro Pro Glu Ser Leu Asn
                  275                 280                 285
Tyr Phe Ile Phe Arg Ser Lys Pro Met Lys His Lys Asp Phe Asn
                  290                 295                 300
Pro Asp Met Pro Phe Leu Asp Leu Met Asp Gln Phe Asp Arg Thr
```

```
                           305                 310                 315
Glu Arg Ile Tyr Tyr Gly Met Glu Asp Ala Ala Ser Glu Lys Glu
                320                 325                 330
Glu Gln Lys Leu Arg Asn Ile Tyr Arg Val Ser Met Ile Glu Glu
                335                 340                 345
Phe Asp Leu Pro Leu Arg Pro Ser Tyr Arg Phe Met Thr Val Ala
                350                 355                 360
Cys Gln Ile Ala Gly Asp Asp Pro Glu Arg Leu Tyr Asp Ile Leu
                365                 370                 375
Arg Arg Asn Ser Gln Leu Pro Glu Glu Leu Met Asp Leu Glu Leu
                380                 385                 390
Asp Gln Leu Thr Asp Lys Gln Leu Glu Gln Leu Asn Glu Arg Ile
                395                 400                 405
Glu Asn Val Lys Asn Trp Leu Arg Leu Tyr Ala Pro Glu Phe Val
                410                 415                 420
Lys Phe Gln Val Gln Glu Leu Pro Asp Val Glu Leu Ser Glu
                425                 430                 435
Pro Gln Leu Lys Phe Leu Gln Asp Val Ala Asp Leu Met Glu Ser
                440                 445                 450
Arg Glu Met Ser Ala Glu Glu Leu His Asp Glu Met Tyr Ser Ile
                455                 460                 465
Leu Arg Arg His Gly Leu Lys Pro Gln Lys Ala Phe Gln Ala Ile
                470                 475                 480
Tyr Arg Val Leu Ile Gly Lys Lys Met Gly Pro Arg Ala Ala Ser
                485                 490                 495
Phe Leu Leu Ser Leu Glu Arg Asp Phe Val Ile Arg Arg Leu Arg
                500                 505                 510
Leu Glu Ala

<210> SEQ ID NO 9
<211> LENGTH: 564
<212> TYPE: PRT
<213> ORGANISM: Rhodobacter capsulatus
<220> FEATURE:
<221> NAME/KEY: lysyl t-RNA synthetase

<400> SEQUENCE: 9

Leu Gly Leu Pro Gln Glu Leu Leu Thr Phe Gln Ala Pro Phe Asn
                 5                  10                  15
Arg Ser Gly Ala Arg Arg Met Gly Arg Pro Asp Glu Asp Leu Thr
                20                  25                  30
Met Thr Thr Leu Arg Asp Ala Ala Met Asn Ser Lys Ala Trp Pro
                35                  40                  45
Phe Glu Glu Ala Arg Arg Val Leu Lys Arg Tyr Glu Lys Ala Pro
                50                  55                  60
Pro Lys Lys Gly His Val Leu Phe Glu Thr Gly Tyr Gly Pro Ser
                65                  70                  75
Gly Leu Pro His Ile Gly Thr Phe Gly Glu Val Ala Arg Thr Thr
                80                  85                  90
Met Ile Arg Arg Ala Phe Glu Ile Ile Ser Asp Ile Pro Thr Arg
                95                  100                 105
Leu Leu Cys Phe Ser Asp Asp Met Asp Gly Met Arg Lys Val Pro
                110                 115                 120
Glu Asn Val Pro Gln Gln Glu Leu Leu Tyr Ala Asn Ile Gln Lys
                125                 130                 135
```

-continued

```
Pro Leu Thr Ala Val Pro Asp Pro Phe Gly Glu Phe Asp Ser Phe
            140                 145                 150
Gly Asn His Asn Asn Ala Met Leu Arg Arg Phe Leu Asp Thr Phe
            155                 160                 165
Gly Phe Glu Tyr Glu Phe Ala Ser Ala Thr Asp Tyr Tyr Lys Ser
            170                 175                 180
Gly Lys Phe Asp Glu Met Leu Met Leu Cys Ala Glu Arg Tyr Asp
            185                 190                 195
Ala Ile Met Ala Ile Met Leu Lys Ser Leu Arg Glu Glu Arg Gln
            200                 205                 210
Gln Thr Tyr Ser Cys Phe Leu Pro Ile His Pro Glu Thr Gly Arg
            215                 220                 225
Val Leu Tyr Val Pro Met Lys His Val Asp Ala Lys Asn Gly Leu
            230                 235                 240
Ile Thr Phe Asp Asp Glu Asp Gly Arg Glu Trp Thr Leu Pro Val
            245                 250                 255
Thr Gly Gly Lys Val Lys Leu Gln Trp Lys Pro Asp Phe Gly Met
            260                 265                 270
Arg Trp Ala Ala Leu Asp Val Asp Phe Glu Met Tyr Gly Lys Asp
            275                 280                 285
His Ser Thr Asn Thr Pro Ile Tyr Asp Gly Ile Cys Glu Val Leu
            290                 295                 300
Gly Gly Arg Lys Pro Glu His Phe Thr Tyr Glu Leu Phe Leu Asp
            305                 310                 315
Asp Gln Gly Gln Lys Ile Ser Lys Ser Lys Gly Asn Gly Leu Thr
            320                 325                 330
Ile Asp Glu Trp Leu Ser Tyr Ala Ala Thr Glu Ser Leu Ser Tyr
            335                 340                 345
Phe Met Tyr Gln Lys Pro Lys Thr Ala Lys Arg Leu Trp Trp Asp
            350                 355                 360
Val Ile Pro Lys Ala Val Asp Glu Tyr His Gln Gln Leu Arg Ala
            365                 370                 375
Tyr Pro Thr Gln Pro Val Glu Lys Gln Ile Asp Asn Pro Val Trp
            380                 385                 390
His Ile His Gly Gly Gln Pro Pro Glu Ser Asn Leu Val Pro
            395                 400                 405
Phe Ala Met Leu Leu Asn Leu Ala Ser Val Ala Gly Ala Ser Asp
            410                 415                 420
Lys Ala Gly Leu Trp Gly Phe Ile Lys Arg Tyr Ala Pro Glu Ala
            425                 430                 435
Thr Pro Glu Thr His Pro Asp Leu Asp Ala Ala Ala Gly Phe Ala
            440                 445                 450
Val Arg Tyr Phe His Asp Phe Val Ala Pro Thr Arg Thr Phe Arg
            455                 460                 465
Leu Pro Ser Asp Lys Glu Arg Ala Ala Met Glu Asp Leu Leu Ala
            470                 475                 480
Arg Leu Lys Ala Leu Pro Ala Thr Asp Leu His Leu Gln Phe Glu
            485                 490                 495
Asp Pro Ser Glu Gly Leu Gln Thr Ile Val Phe Ala Val Gly Thr
            500                 505                 510
Glu His Gly Phe Glu Pro Leu Arg Asp Trp Phe Thr Ala Leu Tyr
            515                 520                 525
```

```
Glu Val Leu Leu Gly Gln Ser Gln Gly Pro Arg Phe Gly Gly Phe
            530                 535                 540

Ile Ala Leu Tyr Gly Val Ser Glu Thr Ile Ala Leu Met Glu Thr
            545                 550                 555

Ala Leu Ala Gly Gly Leu Ile Lys Ala
            560

<210> SEQ ID NO 10
<211> LENGTH: 1602
<212> TYPE: DNA
<213> ORGANISM: Methanococcus maripaludis
<220> FEATURE:
<221> NAME/KEY: lysyl t-RNA synthetase
<223> OTHER INFORMATION: clone described in Example 1

<400> SEQUENCE: 10
```

| | | | |
|---|---|---|---|
| atgcattggg cagatgctac atcggaaaaa atcatgaaaa aaagaaatgc | | | 50 |
| agaggaatac gtggtatcaa gtggaattac tccatctggt cacattcaca | | | 100 |
| ttgggaatgc aagggaaaca ttaactgcag atgcagtttta caagggcatg | | | 150 |
| ctaaaaaaag gtgcagaagc taaattaatt tttattgcgg acgattatga | | | 200 |
| tcctttaaga aaattatatc cattttttacc aaaagaattt gaaaaataca | | | 250 |
| taggaatgcc gttaagtgaa attccatgcc acaaggttg ctgtaaaagc | | | 300 |
| tatgcagatc attttttaat gccgttttta acagtcttg aagatttagg | | | 350 |
| cgttgaaatt actacccata gggcaaatga atgctataaa gctggaatgt | | | 400 |
| acaacgaagc aattataact gcacttgaaa accggttaaa aatcaaagaa | | | 450 |
| cttctcgatt cttaccgaaa agaaccactt gctgataatt ggtatccttt | | | 500 |
| aaacgttgta tgtgaaaaat gcggtaaaat gcacgaaaca aaagttacca | | | 550 |
| gttacaattc tgaagacaaa acaataactt acgtttgtaa atgcggattt | | | 600 |
| gaaaacacgg ttcaaccatt taacggcatt ggaaagcttc cgtggagagt | | | 650 |
| tgactggcct gcaagatgga atatatttgg agttactgct gaaccgatgg | | | 700 |
| gaaaagacca cgcagcgtca ggcggttcat acgatacagg aattaagatt | | | 750 |
| gcaagacaga ttttcaacta ccaagcacca gaaaaaatgg tttacgagtg | | | 800 |
| gattcagtta aaaatcgggg ataaggcaat gccaatgtct tcttcatcag | | | 850 |
| gagttgtatt tgcagtaaaa gactggactg aaatctgcca ccctgaagtt | | | 900 |
| ttaagatttt taatttttaaa aggaaaacca acaaaacaca tagattttga | | | 950 |
| tttaaaagca atttcaaatt tagttgacga ttacgacgaa cttgaaagaa | | | 1000 |
| aatactttga attaatcgaa aaacaaaaaa ctgaagaatt aaacgacaac | | | 1050 |
| gaaaatgaaa aataagtttt atatgaactt gttacaccaa aaatacctga | | | 1100 |
| aagattacca ttacaagttg catacaggtt ctgttcaatt attgctcaga | | | 1150 |
| ttgcactcga taaagaaacc caaaaaattg atatggaaag agtttttcgac | | | 1200 |
| attttgggaa gaaatggata caatccagca gaattttcag aatacgacaa | | | 1250 |
| atcaaggctt gaaaaaaggc tttatatgtc taaaaaatgg gcatccgact | | | 1300 |
| acggtgaaaa tttagaaata aatgattttg agcaagcaaa agagcagtac | | | 1350 |
| gaaacactct cagaagagca aaaagcatgg ttaaaagcat tttccaaaga | | | 1400 |
| agtagaaaat atcgaaattg atgcgaacac gattcacgaa ttgatgtatg | | | 1450 |
| aaactgcaac aaaattaaat cttgcaccaa agaagcgtt tgttgcatca | | | 1500 |

|   |   |
|---|---:|
| tacaaaatac ttctcggtaa aaactacggg ccaaagttag gaagcttttt | 1550 |
| agcatccctt aaaaaagagt tcgtaattgg aagatttaat ttaacagaat | 1600 |
| aa | 1602 |

<210> SEQ ID NO 11
<211> LENGTH: 1563
<212> TYPE: DNA
<213> ORGANISM: Borrelia burgdorferi
<220> FEATURE:
<221> NAME/KEY: lysyl t-RNA synthetase
<223> OTHER INFORMATION: clone described in Example 3

<400> SEQUENCE: 11

|   |   |
|---|---:|
| gtgaaaacag cacactgggc agattttttac gcagaaaaaa taaaaaaaga | 50 |
| aaaaggtcca aaaaacttat acacagtagc atcgggaatt actccatctg | 100 |
| gaactgtgca cattggcaat tttagagaag ttatttcggt agaccttgta | 150 |
| gcaagagcac taagagactc tggatcaaaa gtaaggttta tttattcttg | 200 |
| ggataattac gacgtatttc gaaaagttcc caaaaatatg ccagaacaag | 250 |
| aacttcttac aacttattta agacaagcaa taacaagggt ccctgacaca | 300 |
| agaagccaca aacaagtta tgcaagggct aatgaaattg aatttgaaaa | 350 |
| atatctgcct gtagttggga tcaatcctga attcatcgac caaagcaaac | 400 |
| aatataccag caacgcttat gcaagccaaa taaaatttgc acttgatcat | 450 |
| aaaaagaac tgtctgaagc attaaacgaa tacagaacct caaagcttga | 500 |
| agaaaattgg tatccaatca gtgtatttg tacaaaatgc aatagagaca | 550 |
| caacaactgt aaataattat gacaatcatt actctgttga gtattcatgt | 600 |
| gaatgtggaa atcaagaatc tctagacata agaaccacat gggccattaa | 650 |
| acttccttgg agaatagatt ggcctatgag atggaaatat gaaaaagttg | 700 |
| actttgagcc tgcaggaaaa gaccaccaca gcagtggcgg cagttttgat | 750 |
| acatctaaaa atattgtaaa aattttttcaa ggtagccctc ctgtaacatt | 800 |
| tcaatatgac tttatttcaa taaaaggacg tggtggaaaa atatcctcct | 850 |
| catcgggaga tgtcatatcg ctcaaagatg ttcttgaggt ctatacaccc | 900 |
| gaagtcacaa ggttttttatt tgctgctact aaaccaaata ctgaattttc | 950 |
| aatctcattt gatcttgatg taattaaaat atacgaagat tacgacaaat | 1000 |
| ttgagagaat ctactatgga gtagaagatg taaaagaaga aaaaaaaaga | 1050 |
| gcatttaaaa gaatttacga actatctcaa ccatacatgc caagcaaaag | 1100 |
| aatcccttat caggtcggat tcagacattt aagtgtaatc agtcaaatat | 1150 |
| tgaaaataa tataaataaa attttaaatt acttgaaaaa cgttcaagaa | 1200 |
| gatcaaaaag acaaactaat aaataaaata aattgcgcaa ttaattggat | 1250 |
| aagagatttt gcacccgaag atttcaaatt ttcattaaga tctaaatttg | 1300 |
| ataatatgga atactagaa gaaaatagca aaaagcaat taatgaactt | 1350 |
| ttggattttt taagaaaaa ttttgaagtt gccacagaac aagacattca | 1400 |
| aaacgaaata tataaaattt caagagaaaa taatatagaa cctgctttat | 1450 |
| tttttaaaca aatttataaa attttaattg acaaagaaaa agggcccaaa | 1500 |
| ttagctggat ttatcaaaat aattggtatt gatcgctttg aaaagattac | 1550 |

-continued

```
aagcaaatac gtt                                                           1563

<210> SEQ ID NO 12
<211> LENGTH: 73
<212> TYPE: DNA
<213> ORGANISM: Borrelia burgdorferi
<220> FEATURE:
<221> NAME/KEY: t-RNA synthetase Lys1
<223> OTHER INFORMATION: sequence described in Example 3

<400> SEQUENCE: 12
gggctcatag ctcaggtggt agagcagcgc cctttaagg cgtttgtcgt                    50 aggttcgagt cctactgagc tca                                                73

<210> SEQ ID NO 13
<211> LENGTH: 31
<212> TYPE: DNA
<213> ORGANISM: artificial sequence
<220> FEATURE:
<221> NAME/KEY: KRS1
<223> OTHER INFORMATION: primer employed in note 15
      n = A or C, or G or T, or other

<400> SEQUENCE: 13
ccntgtcccn gaagggntgt ctgtcgaaga g                                       31

<210> SEQ ID NO 14
<211> LENGTH: 30
<212> TYPE: DNA
<213> ORGANISM: artificial sequence
<220> FEATURE:
<221> NAME/KEY: KRS2
<223> OTHER INFORMATION: primer employed in note 15;
      n = A or C, or G or T, or other

<400> SEQUENCE: 14
gcnccngcan gcngcagtga gtctcttncc                                         30

<210> SEQ ID NO 15
<211> LENGTH: 22
<212> TYPE: DNA
<213> ORGANISM: artificial sequence
<220> FEATURE:
<221> NAME/KEY: KRS3
<223> OTHER INFORMATION: primer employed in note 15;
      n = A or C, or G or T, or other

<400> SEQUENCE: 15
atgcatctgg gcngatcgcn ac                                                 22

<210> SEQ ID NO 16
<211> LENGTH: 25
<212> TYPE: DNA
<213> ORGANISM: artificial sequence
<220> FEATURE:
<221> NAME/KEY: KRS4
<223> OTHER INFORMATION: primer employed in note 15

<400> SEQUENCE: 16
gtatcctctt caaactcgtt aggac                                              25
```

CLASS I-TYPE LYSYL-TRNA SYNTHETASE

RELATED APPLICATION DATA

This application is the U.S. National Stage of International Application No. PCT/US98/18968, filed on Sep. 9, 1998, which claims priority benefit of provisional U.S. application Ser. No. 60/058,420, filed on Sep. 10, 1997.

TECHNICAL FIELD OF THE INVENTION

This invention relates to a new class I-type lysyl-tRNA synthetase isolated from archaebacteria and Borrelia.

BACKGROUND OF THE INVENTION

Lysyl-tRNA synthetase (LysRS) is essential for the translation of lysine codons during protein synthesis. In spite of the necessity for this enzyme in all organisms and the high degree of conservation among aminoacyl-tRNA synthetases (1), genes encoding a LysRS homologue have not been found by sequence similarity searches in the genomes of two Archaea, *Methanococcus jannaschii* (2) and *Methanobacterium thermoautotrophicum* (3). This raises the possibility that. LysRS, like the asparaginyl- and glutaminyl-tRNA synthetases (4), is not present, with lysyl-tRNA (Lys-tRNA) synthesized by tRNA-dependent transformation of a misacylated tRNA (5). Alternatively, these organisms may contain a LysRS activity encoded by a gene sufficiently different to those previously identified to prevent its detection by sequence similarity searches.

SUMMARY OF THE INVENTION

This invention confirms the latter hypothesis and provides isolated and purified class I-type lysyl-tRNA synthetase (hereafter sometimes denoted herein as LysRSI) and active fragments and variants thereof, DNA and RNA sequences encoding class I-type lysyl-tRNA synthetase (and biological equivalents and fragments thereof), and methods for screening for class I-type lysyl-tRNA synthetase inhibitors for medical and veterinary use. It further provides methods for screening for infection of an organism by microorganisms expressing class I-type lysyl-tRNA synthetase.

DESCRIPTION OF THE FIGURES

FIG. 2 shows alignment of class I-type lysyl-tRNA synthetase amino acid sequences. The Figure uses the following abbreviations for the amino acid residues: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val, W, Trp; and Y, Tyr. The sequences were aligned using the CLUSTAL W program (20). The sequences shown are from *Pyrococcus fuliosus* (PF, SEQ ID NO: 1), *Pyrococcus horikoshii* (PH, SEQ ID NO: 2), *Borrelia burgdorferi* (BB, SEQ ID NO: 3), *Treponema pallidum* (TP, SEQ ID NO: 4), *Methanococcus jannaschii* (MJ, SEQ ID NO: 5), *Methanococcus maripaludis* (MM, SEQ ID NO: 6, expressed in Example 1 as a construct with an extra methionine at the end), *Archaeoglobus fulgidus* (AF, SEQ ID NO: 7), *Methanobacterium thermoautotrophicum* (MT, SEQ ID NO: 8) and *Rhodobacter capsulatus* (RC, SEQ ID NO: 9).

DETAILED DESCRIPTION OF THE INVENTION

Figure 1:
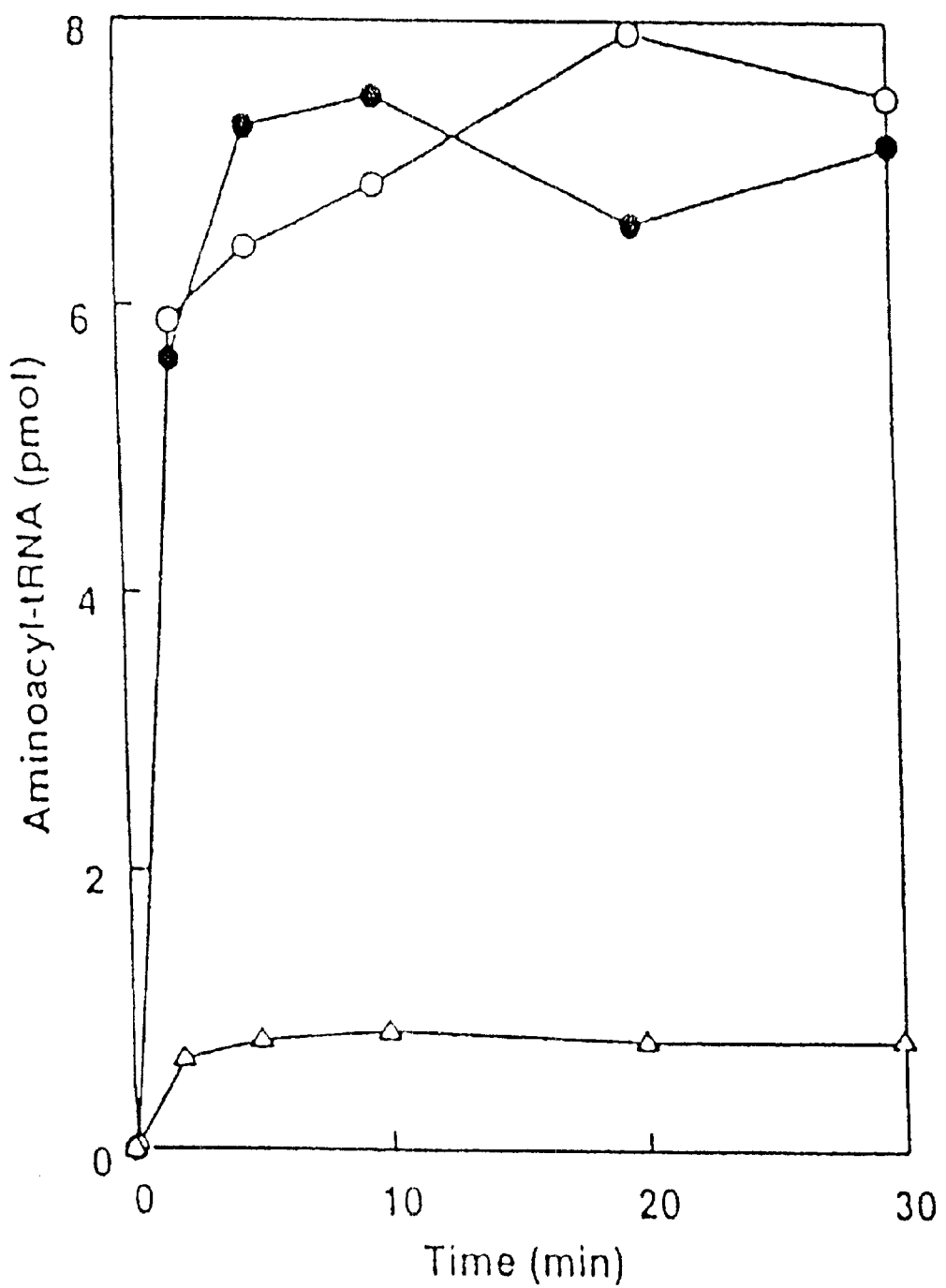
FIG. 1 is a line graph providing data related to the direct attachment of lysine to tRNA by *M. maripaludis* protein extracts. Aminoacylation reactions were performed as described in the Examples that follow in the presence of 200 µg RNA-free total protein prepared from an S160 extract in a reaction volume of 130 µl. Aliquots (20 µl) were periodically removed and analyzed. Reactions were performed in the presence of: open circles, 20 µM ($^{14}$C)lysine; closed circles, 20 µM ($^{14}$C)lysine and the 19 canonical amino acids (800 µM ($^{12}$C)) except for lysine; triangles, 20 µM ($^{14}$C) lysine and 800 µM ($^{12}$C)lysine.

This invention is based upon the isolation and sequencing of a eury-archaeal class I-type lysyl-tRNA synthetase distinguishable from class IIc-type lysyl-tRNA synthetase found in bacteria and eukarya, and the identification of genes for analogous sequences in other microorganisms, including microorganisms of medical and veterinary importance.

The sequencing of euryarchaeal genomes had suggested that the essential protein lysyl-tRNA synthetase (LysRS) is absent from such organisms. However, as summarized above and set out in the Examples that follow, a single 62-kD protein with canonical LysRS activity was purified from *Methanococcus maripaludis*, and the gene that encodes it, cloned. The predicted amino acid sequence of *M. maripaludis* LysRS is similar to open reading frames of unassigned function in both *Methanobacterium thermoautotrophicum* and *Methanococcus jannaschii*, but is unrelated to canonical LysRS proteins reported in eubacteria, eukaryotes, and the Crenarchaeote *Sulfolobus solfataricus*. The presence of amino acid motifs characteristic of the Rossmann dinucleotide binding domain identify *M. maripaludis* LysRS as a class I aminoacyl-tRNA synthetase, in contrast to the known examples of this enzyme, which are class II synthetases.

Analysis of the genomic sequences of the bacterial pathogen *Borrelia burgdorferi*, the causative agent of Lyme disease, indicated the presence of an open reading frame with over 55% similarity at the amino acid level to archaeal class I-type lysyl-tRNA synthetase. In contrast, no coding region with significant similarity to any class-II type lysyl-tRNA synthetase could be detected. Heterologous expression of this open reading frame in *Escherichia coli* led to the production of a protein with canonical lysyl-tRNA synthetase activity in vitro. Analysis of *B. burgdorferi* mRNA showed that the lysyl-tRNA synthetase encoding gene is constitutively expressed in vivo. The data indicate that, like the archaeabacteria described above, *B. burgdorferi* also contains a functional class I-type lysyl-tRNA synthetase, again in contrast to most other bacteria and eukaryotes which contain class II-type enzymes.

The kinetic parameters of *B. burgdorferi* lysyl-tRNA synthetase were further assessed by amplifying and cloning the gene for *B. burgdorferi* tRNA-Lys1 and using the gene to make a tRNA in vitro using standard techniques. The rate of formation of Lys-tRNA was found to be the same with synthetic substrate as observed for other class I-type lysyl-tRNA synthetases with tRNAs synthesized in vivo.

This invention thus provides isolated and purified class I-type lysyl-tRNA synthetase (hereafter sometimes denoted herein as LysRSI) and active fragments and variants thereof, DNA and RNA sequences encoding class I-type lysyl-tRNA synthetase (and biologically equivalents and fragments thereof), and methods for screening for class I-type lysyl-tRNA synthetase inhibitors for medical and veterinary use. It further provides methods of detecting infection of an organism which expresses class II-type lysyl-tRNA synthetase by a microorganism expressing class I-type lysyl-tRNA synthetase.

Figure 2:
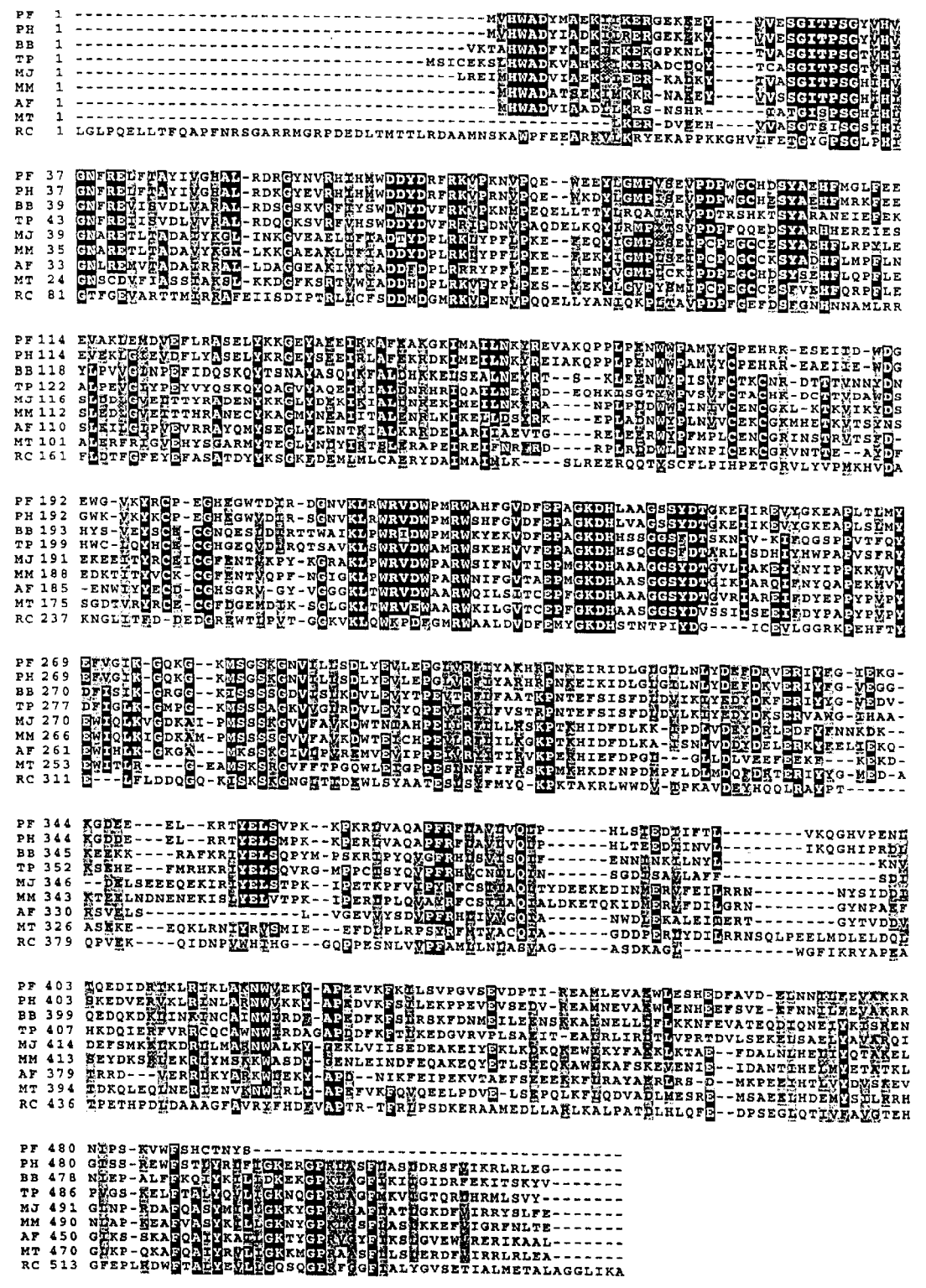

In one embodiment, the invention provides purified and isolated DNA encoding the deduced LysRSI polypeptide set out as MM in FIG. 2 (SEQ ID NO: 6), degenerate and complimentary sequences to SEQ ID NO: 10, and sequences that hybridize under stringent conditions with the sequence. In another embodiment, the invention provides purified and isolated DNA encoding the deduced LysRSI polypeptide set out as BB in FIG. 2 (SEQ ID NO: 3), degenerate and complementary sequences to SEQ ID NO: 11, and sequences that hybridize under stringent conditions with the sequence. Also encompassed by this invention are cloned sequences defining LysRSI, which can then be used to transform or transfect a host cell for protein expression using standard means. Also encompassed by this invention are DNA sequences homologous or closely related to complementary DNA described herein, namely DNA sequences which hybridize to LysRSI cDNA, particularly under stringent conditions that result in pairing only between nucleic acid fragments that have a high frequency of complementary base sequences, and RNA corresponding thereto. In addition to the LysRSI-encoding sequences, DNA encompassed by this invention may contain additional sequences, depending upon vector construction sequences, that facilitate expression of the gene. Also encompassed are sequences encoding synthetic LysRSI peptides or polypeptides exhibiting enzymatic activity and structure similar to isolated or cloned LysRSI. These are referred to herein as "biological equivalents or variants," and in some embodiments have at least about 50%, preferably at least about 60% to 85%, and more preferably, at least about 90% sequence homology with LysRSI.

Because of the degeneracy of the genetic code, a variety of codon change combinations can be selected to form DNA that encodes LysRSI of this invention, so that any nucleotide deletion(s), addition(s), or point mutation(s) that result in a DNA encoding the protein are encompassed by this invention. Since certain codons are more efficient for polypeptide expression in certain types of organisms, the selection of gene alterations to yield DNA material that codes for the protein of this invention are preferably those that yield the most efficient expression in the type of organism which is to serve as the host of the recombinant vector. Altered codon selection may also depend upon vector construction considerations.

DNA starting material which is employed to form DNA coding for LysRSI peptides or polypeptides of this invention may be natural, recombinant or synthetic. Thus, DNA starting material isolated from cultures of microorganisms, constructed from oligonucleotides using conventional methods, obtained commercially, or prepared by isolating RNA coding for LysRSI, and using this RNA to synthesize single-stranded cDNA which is used as a template to synthesize the corresponding double stranded DNA, can be employed to prepare DNA of this invention.

DNA encoding the peptides or polypeptides of this invention, or RNA corresponding thereto, are then inserted into a vector, and the recombinant vector used to transform a microbial host organism. Example host organisms useful in the invention include, but are not limited to, bacterial (e.g., *E. coli* or *B. subtilis*), yeast (e.g., *S. cerevisiae*), mammalian (e.g., mouse fibroblast or other cell line) or insect (e.g., baculovirus expression system) cells. This invention thus also provides novel, biologically functional viral and circular plasmid RNA and DNA vectors incorporating RNA and DNA sequences describing LysRSI or functional LysRSI fragments generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or. cellular membrane fractions yields the desired products.

The present invention thus provides for the total and/or partial manufacture of DNA sequences coding for LysRSI, and including such advantageous characteristics as incorporation of codons preferred for expression by selected non-mammalian hosts, provision of sites of cleavage by restriction endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of LysRSI analogues which differ from the form specifically described herein in terms of identity or location of one or more amino acid residues (i.e., deletion analogues containing less than all of the residues specified for the protein, and/or substitution analogues wherein one or more residues are added to a terminal or a medial portion of the polypeptide), and which share or alter the biological properties of LysRSI described herein.

DNA (and RNA) sequences of this invention code for all sequences useful in securing expression in procaryotic or eucaryotic host cells of peptide or polypeptide products having at least a part of the primary structural conformation, and one or more of the biological properties of LysRSI which are comprehended by: (a) the DNA sequences encoding LysRSI as described herein, or complementary strands; (b) DNA sequences which hybridize (under hybridization conditions) to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of LysRSI included there in, and sequences encoding RNA, fragments thereof, and analogues wherein RNA or DNA sequences may incorporate codons facilitating transcription or RNA replication of messenger RNA in non-vertebrate hosts.

The invention also provides the LysRSI peptides or polypeptides encoded by the above-described DNA and/or RNA, obtained by isolation or recombinant means, as well as the polypeptide set out as MM in FIG. 2 (SEQ ID NO: 6), BB in FIG. 2 (SEQ ID NO: 3), and their structural analogues. The invention correspondingly provides peptide mimics such as peptide fragments of LysRSI and functionally equivalent counterparts that demonstrate its enzymatic activity. For example, alterations in known sequences can be performed to enhance enzyme activity measurements or other properties desirable for use in screening methods and the like.

Isolation and purification of peptides and polypeptides provided by the invention are by conventional means including, for example, preparative chromatographic separations such as affinity, ion-exchange, exclusion, partition, liquid and/or gas-liquid chromatography; zone, paper, thin layer, cellulose acetate membrane, agar gel, starch gel, and/or acrylamide gel electrophoresis; immunological separations, including those using monoclonal, polyclonal, and/or fusion phage antibody preparations; and combinations of these with each other and with other separation techniques such as centrifugation and dialysis, and the like.

It is an advantage of the invention that the isolation and purification of LysRSI provides a polypeptide that is useful in screens for LysRSI inhibitors. LysRSI inhibitors are typically identified in screening assays when test compounds inhibit a functional property of the enzyme in an assay. By "LysRSI inhibitor" is meant any inhibitor of LysRSI function, antibodies to LysRSI or LysRSI functional fragments that inhibit enzymatic activity, receptor antagonists, and the like, and mixtures thereof. Inhibitors that do not inhibit class II-type lysyl-tRNA synthetase are particularly preferred. Any standard assay such as that described in the Examples that follow can be used to screen large collections of test compounds, or screen monoclonal, polyclonal, or fusion phage antibodies that inhibit enzymatic activity. Mixtures of inhibitors can also be employed. For example, the invention provides a method for screening for the presence or absence of class I-type lysyl-tRNA synthetase enzyme inhibition by a test sample comprising incubating the test sample with the enzyme and its substrates for a time under conditions sufficient to observe enzymatic activity in a control incubation of enzyme and substrates, and determining inhibition by observation of decreased enzymatic activity in the incubation with test sample in comparison to the control. In addition to using lysine, assays of the invention typically employ naturally-occuring isolated tRNA, total tRNA, synthetic substrates such as that prepared in the examples that follow, and fragments, variants, and mixtures thereof.

In addition to screening methods for enzymatic activity, the invention further provides screening methods for testing compounds, antibodies and the like, as inhibitors of LysRSI synthesis or stability, and adjunct compounds that enhance uptake, minimize side effects, and other properties required of inhibitors for certain medical and veterinary applications. The invention thus provides a way to identify compounds which can be used to inhibit LysRSI for therapeutic purposes as well as adjunct compounds. The unique sequence information is therefore useful for the development of therapeutically relevant compounds.

It is a further and important advantage of the invention that in all species observed to exhibit lysRSI activity do not exhibit the type II-type lysyl tRNA synthetase (LysRSII) activity common in most other species, including animals. Because the enzyme is essential for protein synthesis in the organisms, inhibitors and adjunct compound to be useful in screening methods of the invention to inhibit lysRSI activity can be used therapeutically to treat and control infectious agents exhibiting lysRSI activity Infectious agents include, but are not limited to, *Borrelia burgdorferi*, the causative agent of Lyme disease; other Borrelia that cause various types of relapsing fever; *Treponema pallidum*, the causative agent of syphilis, Leptospira and other spirochetes causing infectious hepatitis and various leptospiroses; as well as other pathogenic microorganisms having lysRSI and not lysRSII. Because of the fundamental difference in the lysyl-tRNA synthetase enzymes between pathogen and host, the pathogen can be specifically targeted and its replication, stopped without causing harm to the host For certain infections and pathological conditions, the invention therefore provides treatments that represent a marked improvement over broad-spectrum antibiotics that kill beneficial organism as well as pathogens.

As summarized above, the invention also provides valuable diagnostic screens. In a typical screen, a biological sample is obtained from an organism such as a mammal that is subject to infection by a microorganism expressing class I-type lysyl-tRNA synthetase. The presence of infection is determined by observation of class I-type lysyl-tRNA synthetase activity in the sample using any type of assay described above, or by observation of the polypeptide in the sample by standard means such as an ELISA, RIA, fluorochrome tag, and the like which typically employ an antibody or antibody fragment, including fusion phage as well as monoclonal antibodies, to detect the presence of the polypeptide.

Any type of biological sample suitable for an enzyme assay or polypeptide detection method may be employed in diagnostic screens according to the invention. Typical preferred samples are liquids. For disease detection in medical or veterinary patients or mammalian sampling of disease host reservoirs, plasma and serum may be employed, as can blood, saliva, tears, semen, amnionic fluid, and biopsy tissue. For disease detection in vector populations such as ticks in Borrelia screens, typical samples are ground arthropods or arthropod tissues. The invention thus provides new assays for Lyme disease, syphilis, and other pathological conditions caused by microorganisms expressing class I-type lysyl-tRNA synthetase.

Alternatively, polynucleotide sequences encompassed by the invention such as SEQ ID NOs 10 and 11 can be used in the design of probes for the detection of infection using RNA or DNA analysis. Identification of sequences encoding class I-type lysyl-tRNA synthetase in biological samples obtained from cultures, vectors, hosts, or patients indicates the presence of infection by the pathological microorganism.

EXAMPLES

The following examples are presented to further illustrate and explain the present invention and should not be taken as limiting in any regard.

Example 1

To investigate the formation of Lys-tRNA in cell-free extracts prepared from *M. maripaludis*, ($^{14}$C) lysine and homologous total TRNA were used as substrates (6). Amino acid analysis of the $^{14}$C labeled aminoacyl-tRNA produced in this reaction (7) indicated that lysine was directly acylated onto tRNA and therefore that Lys-tRNA was not the product of a tRNA-dependent amino acid transformation. This was confirmed by the observation that ($^{14}$C)Lys-tRNA synthesis was inhibited by only one of the 20 canonical amino acids, lysine (FIG. 1). This is consistent with the presence of LysRS, since Lys-tRNA synthesis via a mischarged tRNA would result in a non-labeled amino acid other than lysine being able to inhibit lysylation of tRNA. On the basis of these observations LysRS from *M. maripaludis* was purified. By standard chromatographic procedures (8), a single 62-kD protein was isolated, which was purified to homogeneity as judged by both silver staining after denaturing polyacrylamide gel electrophoresis (SDS-PAGE) and the appearance of a single symmetrical peak during size exclusion chromatography. The LysRS activity eluted as a single discrete fraction during all purification steps, indicating that *M. maripaludis* contains only a single LysRS activity. The enzyme could acylate unfractionated tRNA with lysine to the same degree as the *M. maripaludis* crude extract (FIG. 1), confirming that the purified protein is LysRS. In kinetic characterizations of our LysRS for the aminoacylation of *M. maripaludis* total tRNA with lysine (9), a $K_M$ for lysine of 2.2 μM and a $k_{cat}$ of 1.6 s$^{-1}$ were observed, values comparable to other LysRS proteins (10). Investigation of the species-specificity of Lys-tRNA formation in cell-free extracts showed reactivity between tRNA and RNA-free protein extracts prepared from *E. coli, M. thermoautotrophicum*, and *M. maripaludis* (11). The only exception was *M. maripaludis* tRNA, which is not a substrate for the *E. coli* enzyme, suggesting that it may lack 2-thiouridine and its derivatives which are required for the LysRS·tRNA$^{Lys}$ interaction (12). These modified nucleotides have previously been detected at position 34 in all known tRNA$^{Glu}$ and tRNA$^{Lys}$ isoacceptors (13). In that these modifications are critical for recognition of the tRNA$^{Lys}$ anticodon by LysRS (12), their possible absence suggests that tRNA recognition by the *M. maripaludis* enzyme is substantially different from known examples and may explain the inability of an *E. coli* extract to aminoacylate *M. maripaludis* tRNA with lysine.

Figure 3:
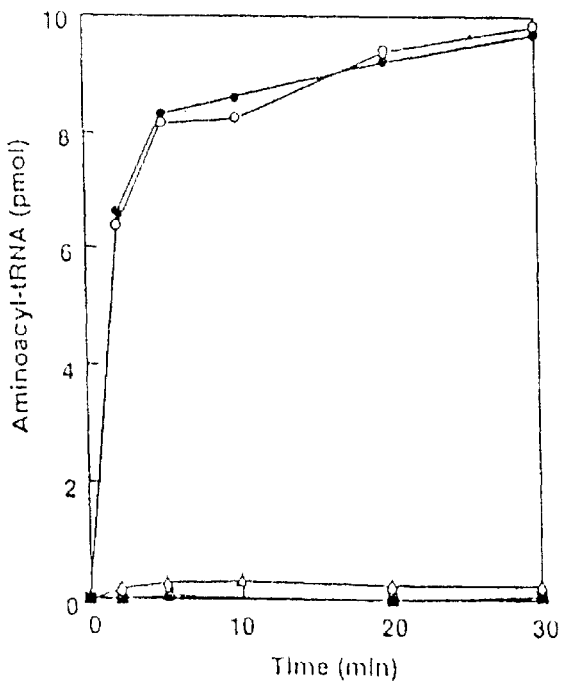
FIG. 3 is a line graph showing aminoacylation of *M. maripaludis* tRNA by purified *M. maripaludis* His$_6$-LysRS. Aminoacylation reactions were performed as described (20 µl samples) in the presence of 20 nM enzyme and the following amino acids: open circles, 20 µM ($^{14}$C)lysine; closed circles, 20 µM ($^{14}$C)lysine and the 19 canonical amino acids (800 µM ($^{12}$C)) except for lysine; triangles, 20 µM ($^{14}$C)lysine and 800 µM ($^{12}$C)lysine. The squares represent an aminoacylation reaction performed with 20 µM ($^{14}$C)lysine and 50 nM control protein preparation (His$_6$-glutamyl-tRNA reductase). The level of product formation at 30 minutes indicates that the *M. Maripaludis* total tRNA preparation contains approximately 32 pmol lysine tRNA per A$_{250}$ unit, in good agreement with the value for commercial *E. coli* total tRNA reagents (40 pmol/A$_{250}$, Boehringer Mannheim).

A portion (22 amino acid residues) of the NH$_2$-terminal sequence of LysRS was determined by protein analysis and the sequence was used to clone lysS, the LysRS-encoding gene (SEQ ID NO: 10). This amino acid sequence is homologous to the NH$_2$-terminus of a predicted protein coding region (MJ0539) in the *M. jannaschii* genome and one in *M. thermoautotrophicum*, but finds no homology elsewhere in any public database. The coding sequence MJ0539 has been tentatively identified as a putative aminoacyl tRNA-synthetase (14). The NH$_2$-terminal sequence was used in conjunction with a conserved internal region in the *M. jannaschii* and *M. thermoautotrophicum* open reading frames (ORFs) to clone by the polymerase chain reaction (PCR) a 450 bp fragment of *M. maripaludis* lysS from genomic DNA. This fragment was $^{32}$P-labeled and used to isolate a DNA fragment containing the 3'-terminal 1293 bp of the lysS gene from a genomic library. The remainder of lysS (306 bp) was cloned by PCR from genomic DNA with a 5'-primer based on the NH$_2$-terminal amino acid sequence of LysRS. After being sequenced, the two portions of lysS were used to derive a full-length clone (15). The lysS gene is 1599 bp in length and encodes a 61.3-kD protein, in good agreement with the molecular mass deduced for the native protein from SDS-PAGE (FIG. 2). To confirm the identity of the cloned gene as lysS, it was subcloned into pET15b, which allowed the overproduction and subsequent chromatographic purification of *M. maripaludis* LysRS as a hexahistidine (His$_6$) fusion protein (16). This purified His$_6$-LysRS was able to aminoacylate with lysine *M. maripaludis* total tRNA to the same extent and at the same rate as the native enzyme (FIG. 3).

The predicted amino acid sequence of *M. maripaludis* LysRS is homologous to putative proteins in *Archaeoglobus fulgidus* (14), *M. thermoautotrophicum* and *M. jannaschii* but otherwise appears to have little or no similarity to any known sequences outside of the Euryarchaeota, including that for LysRS from the Crenarchaeon *Sulfolobus solfataricus* (a normal class II enzyme). The only exception is a putative ORF in the Crenarchaeon Cenarchaeum sp. which shares approximately 28% amino acid identity with the euryarchaeal LysRS protein herein described, including extensive homology in the regions containing the HIGN (residues 37 to 40 of SEQ ID NO: 3) and KISSS (residues 280 to 285 of SEQ ID NO: 3) motifs. Thus, although this protein performs the enzymatic function of a conventional LysRS, the specific esterification of tRNA with lysine, catalysis is accomplished in the context of an amino acid landscape that lacks any sequences corresponding to motifs 1, 2 or 3 (17), which are found in known LysRS proteins now classified as class II aminoacyl-tRNA synthetases (24). Based on extensive similarities in their NH$_2$-terminal domains, LysRS, aspartyl- (AspRS), and asparaginyl- (AsnRS) tRNA synthetases were grouped as paralogous enzymes in subclass IIb (18). However, the euryarchaeal LysRS bears no similarity to AspRS (for the latter is normal) and AsnRS is absent, which leaves AspRS as the only member of this subclass. Thus there would appear to be considerably more evolutionary variation of the aminoacyl-tRNA synthetases than previously thought, a proposal supported by the apparent absence of a recognizable cysteinyl-tRNA synthetase in at least some of the Archaea (2, 3) and the existence in the *M. jannaschii* genome of an ORF (MJ1660) encoding an unidentified class II aminoacyl-tRNA synthetase similar to the α-subunit of phenylalanyl-tRNA synthetase (14).

The euryarchaeal LysRS proteins show variations of the HIGN (residues 37 to 40 of SEQ ID NO: 3) and KISSS (residues 280 to 285 of SEQ ID NO: 3) nucleotide binding motifs (FIG. 2) characteristic of class I aminoacyl-tRNA synthetases. The occurrence of such sequence motifs has been correlated by structural studies with the topology of the catalytic domain, class I aminoacyl-tRNA synthetases containing a Rossmann fold and class II an anti-parallel β sheet. The fact that euryarchaeal LysRS proteins show the defining motifs of class I aminoacyl-tRNA synthetases forces the unexpected conclusion that the catalytic domains of these enzymes are structurally unrelated to those of their bacterial, eukaryotic, and even certain crenarchaeal counter-parts which belong to class II (19). Phylogenetic analysis of an overall class I alignment (20) did not indicate any unequivocal specific relationship between euryarchaeal LysRS and any other class I aminoacyl-tRNA synthetase. Thus it is presently unclear whether the euryarchaeal-type LysRS was present in the last common ancestor or arose later through recruitment of another class I enzyme within the archaea. This is surprising because LysRS (like other aminoacyl-tRNA synthetases (20)) is conserved through evolution both in the other living kingdoms and in certain Crenarchaeota. To date, archaeal LysRS appears to represent the only known example of class switching among aminoacyl-tRNA synthetases and confirms the unexpected evolutionary origin of euryarchaeal LysRS. LysRS has so far been detected in both major branches of the Archaea; four euryarchaeotes (FIG. 3) and two crenarchaeotes, Cenarchaeum sp. and *S. solfataricus*. All show the unexpected class I LysRS except for *S. solfataricus*, which, like all other examples contains a class II LysRS (whether it also contains a class I LysRS is not known). This dichotomy is sufficiently complex and the number of archaeal examples are sufficiently small that speculation concerning LysRS evolution is not warranted at this stage. However, our data do cast doubt on previous evolutionary proposals based on the presumption of constancy of distribution of any given aminoacyl-tRNA synthetase. The observation that archaeal LysRS is a class I aminoacyl-tRNA synthetase also represents a functional demonstration of non-orthologous displacement (21) of a gene required for a core process in gene expression. It differs, for example, from archaeal histone-like proteins (22) and the recently discovered DNA topoisomerase VI of

*Sulfolobus shibatae* (23), as these enzymes both have eukaryotic homologues of known function.

Example 2

Figure 4:
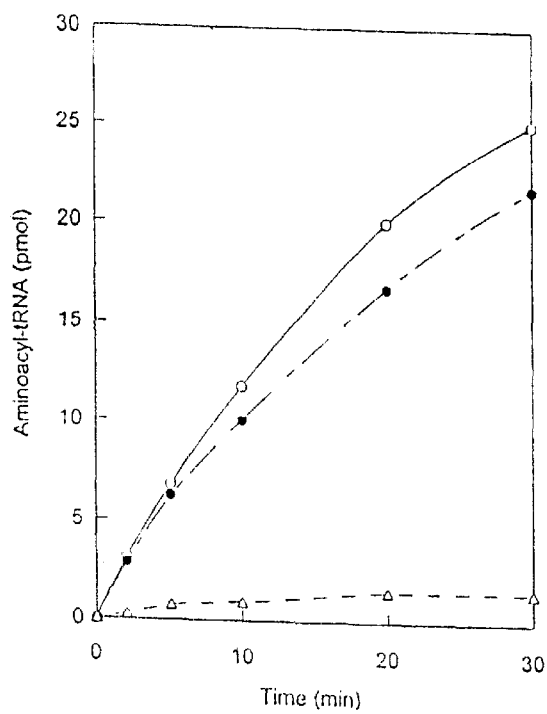
FIG. 4 is a line graph showing aminoacylation of *E. coli* tRNA by purified *B. burgdorferi* His$_6$-LysRS. Aminoacylation reactions were performed as described (20 µl samples) in the presence of 20 nM enzyme and the following amino acids: open circles, 20 µM ($^{14}$C)lysine; closed circles, 20 µM ($^{14}$C)lysine and the 19 canonical amino acids (800 µM ($^{12}$C)) except for lysine; triangles, 20 µM ($^{14}$C)lysine and 800 µM ($^{12}$C)lysine.

Preliminary analysis of the genomic sequence of the bacterial pathogen *Borrelia burgdorferi*, the causative agent of Lyme disease, indicated the presence of an open reading frame encoding a protein with over 55% similarity at the amino acid level to the class I-type lysyl-tRNA synthetase of *Methanococcus maripaludis* (27) described in Example 1 above and shown in FIG. 2. In contrast, no coding region with significant similary to any class-II type lysyl-tRNA synthetase could be detected. In order to test the functionality of the protein encoded by this putative open reading frame (BblysS), the corresponding nucleotide sequence was amplified from a Borrelia total DNA preparation by the polymerase chain reaction. The product of this reaction was then subcloned into the vector pET15b as described in Example 1 above to facilitate heterologous expression of this open reading frame in *E. coli*. The *E. coli* strain BL21(DE3) was then transformed with this vector (pET15b-BblysS) and grown under standard conditions. Isopropyl β-D-thiogalactopyranoside-induced expression of the BblysS gene led to the production of a protein of the expected size (63.2 kD). This protein was then purified to electrophoretic homogeneity by standard chromatographic procedures. The protein displayed canonical lysyl-tRNA synthetase activity in vitro (FIG. 4), confirming that the BblysS gene encodes a functional homologue of *Methanococcus maripaludis* lysyl-tRNA synthetase. Thus, the lysyl-tRNA synthetases of *Borrelia burgdorferi* and *Methanococcus maripaluis* share a common origin. This result is surprising as all previously characterized bacterial and lysyl-tRNA synthetases are class II-type synthetases.

Example 3

In order to characterize the kinetic parameters of *Borrelia burgdorferi* lysyl-tRNA synthetase encoded in SEQ ID NO: 11, the nucelotide sequence encoding *B. burgdorferi* tRNALys1 (SEQ ID NO: 12) was amplified from a total DNA preparation by the polymerase chain reaction. The product was then subcloned into the vector pUC119 such that it was under transcriptional control of the T7 RNA polymerase promoter. The *E. coli* strain DH5α was then transformed with this vector (pUC119-Bb tRNALys1) and grown under standard conditions with ampicillin selection. The plasmid (pUC119-Bb tRNALys1) was then purified by standard procedures and subjected to enzymatic digestion by the restriction endonuclease BstN1. After purification by standard procedures, the cleaved plasmid DNA was used as a template for T7 RNA polymerase directed in vitro transcription. The RNA transcript produced by this reaction was then purified under denaturing conditions and refolded. This RNA transcript, which corresponds to an unmodified form of *Borrelia burgdorferi* tRNALys1, was then used for in vitro aminoacylation assays as described in Example 2 above. The rate of formation of Lys-tRNA was found to be the same with this synthetic substrate as previously observed for other class I-type lysyl-tRNA synthetases with tRNAs synthesized in vivo.

REFERENCES AND NOTES

1. J. Chen, A. Brevet, M. Lapadat-Taplosky, S. Blanquet, P. Plateau, *J. Bacteriol* 176, 2599 (1994); F. Agou, S. Quevillon, P. Kerjan, M. T. Latreille, M. Mirande, *Biochemistry* 35, 15322 (1996); C. W. Sensen et al., *Mol. Microbiol.* 22, 175 (1996).
2. C. J. Bult et al., *Science* 273, 1058 (1996).
3. D. Smith et al., *J. Bacteriol.* (1997).
4. A. W. Curnow, M. Ibba, D. Söll, *Nature* 382, 589 (1996).
5. M. Ibba, A. W. Curnow, D. Söll, *Trends Biochem. Sci.* 22, 39 (1997).
6. Frozen *M. maripaludis* cells were resuspended in one volume of buffer A (25 mM Hepes, pH 7.2, 1 mM $MgCl_2$, 30 mM NaCl, 5 mM dithiothreitol (DTT), 4 mM 2-mercaptoethanol, 10% glycerol), sonicated, and centrifuged at 160,000 g for 3 hours. This extract (S160) was then exchanged into fresh buffer A and applied to a Q-Sepharose Fast Flow column (all chromatography columns were from Pharmacia). The major protein fraction was then eluted with buffer A containing 300 mM NaCl. Under these conditions, RNA remains bound to the column. The protein extract was then concentrated by ammonium sulfate precipitation, and resuspended and exchanged back into buffer A. *M. maripaludis* and *M. thermoautotrophicum* total tRNA were prepared by standard methods; *E. coli* total tRNA was from Boehringer Mannheim. Aminoacylation reactions were performed at 37° C. in 100 mM Hepes, pH 7.2, 50 mM KCl, 10 mM $MgCl_2$, 5 mM ATP, 5 mM DTT, BSA at 0.1 mg/ml, 20 $\mu$M ($^{14}$C-U)lysine (317 $\mu$Ci/$\mu$mol; NEN Dupont), and tRNA at 1 mg/ml.
7. For the analysis of the 3'-esterified amino acid, samples were removed from the aminoacylation reaction, and the attached amino acid was recovered as described (4). Samples were then applied to cellulose thin layer chromatography (TLC) plates which were developed in a mixture of methanol (6 parts):chloroform (6 parts) :ammonium hydroxide (2 parts):water (1 part) (E. von Arx, and R. Neher, *J. Chromatog.* 12, 329 (1963)). $^{14}$C-labeled amino acids were visualized by phosphorimager and internal standards by ninhydrin staining.
8. Frozen cells (20g) were used to prepare an S160 extract as described above, from which the major protein fraction was then separated by ammonium sulfate precipitation. This fraction was dialyzed and applied to a Q-Sepharose Fast Flow column which was then developed with an NaCl gradient (0 to 300 mM). LysRS-containing fractions were pooled, dialyzed, and then fractionated by anion exchange chromatography with a Mono-Q column. Active fractions were again pooled and dialyzed and the pH was adjusted from 7.2 to 6, and the fractions applied to a Mono-S cation exchange column that was developed with an NaCl gradient (0 to 250 mM). The LysRS containing samples were pooled and concentrated before they were applied to a Superose 12 gel filtration column (buffer A, pH 7.2). The LysRS fractions from this final step were judged to be pure by silver staining after SDS-PAGE. Approximately 0.4 mg of LysRS were obtained by this procedure.
9. For the determination of kinetic parameters, LysRS was added to a final concentration of 5 nM and the lysine concentration was varied in the range 0.2 to 5 times the $K_M$. Sampling and quantification were as described (K.-W. Hong et al., *EMBO J.* 15, 1983 (1996)).
10. W. Freist and D. H. Gauss, *Biol. Chem. Hoppe Seyler* 376, 451 (1995).
11. Significant lysylation represents at least 25% of the activity observed in the corresponding homologous system.
12. K. Tamura, H. Himeno, H. Ashahara, T. Hasegawa, M. Shimizu, *Nucleic Acids Res.* 20, 2335 (1992).
13. K. Watanabe et al., *Nucleic Acids Res.* 22, 79 (1994); G. R. Björk, in tRNA: *Structure, Biosynthesis, and Function*, D. Söll and U. L. RajBhandary, Eds. (ASM Press, Washington, D.C., 1995), p.165; S. Cusack, A. Yaremchuk, M. Tukalo, *EMBO J.* 15, 6321 (1996).

14. A. R. Kerlavage, et al. The complete genome sequence of the hyperthermophilic, sulphate-reducing aracheon *Archaeoglobus fulgidus*. The Institute for Genomic Research, Rockville, Md. 20850. Retrieved from the Internet: <URL: http://www.tigr.org/tigr-scripts/CMR2/GenomePage3.spl?database=gaf>. Sequence published in *Nature* 390:364–370 (1997); erratum in *Nature* 394: 101 (1998).

15. An internal fragment of the lysS gene was cloned from *M. maripaludis* genomic DNA by2 PCR with the primers CCNTG(TC)CCNGA(AG)GGNTG(TC)TG(TC)GA(AG)AG (KRS1, SEQ ID NO: 13) and GCNCCNG(CA)NGCNGCAG(TG)(AG)TC(TC)TTNCC (KRS2, SEQ ID NO: 14). This probe was then $^{32}$P-labeled and hybridized to a *M. maripaludis* genomic Zap Express (Stratagene) λ library. This allowed isolation of the 3' end of lysS (over 80% of the gene). The remaining 5' region was cloned by PCR from genomic DNA using as primers KRS2 and KRS3 (ATGCA(TC)TGGGCNGA(TC)GCNAC, SEQ ID NO: 15). Both strands of these fragments were sequenced by dye labeling, and no differences were found in the overlapping regions. The complete lysS ORF was then generated by overlap-extension PCR using the two cloned fragments as templates with the primers KRS3 and KRS4 (GTATCCTCTTCAAACTCGTTAGGAC, SEQ ID NO: 16), which is complementary to a sequence 3' from the stop codon of lysS.

16. For expression in *E. coli*, *M. maripaludis* lysS was subcloned into pET15b (Invitrogen) and then used to transform the strain BL21 (DE3) (W. F. Studier, A. H. Rosenberg, J. J. Dunn, J. W. Dudendorf, *Methods Enzymol.* 85, 60 (1990)). This transformation allowed the production of His$_6$-LysRS, which was subsequently purified by nickel-affinity chromatography (Qiagen) followed by gel filtration with a Superose 12 column (8).

17. G. Eriani, M. Delarue, O. Poch, J. Gangloff, D. Moras, *Nature* 347, 203 (1990).

18. S. Cusack, *Nature Struct. Biol.* 2, 824 (1995).

19. S. Onesti, A. D. Miller, P. Brick, *Structure* 3, 163 (1995).

20. A phylogenetic tree was constructed by the maximum parsimony method (J. R. Brown and W. F. Doolittle, *Proc. Natl. Acad. Sci. U.S.A.* 92, 2441 (1995); G. M. Nagel and R. F. Doolittle, *J. Mol. Evol.* 40, 487 (1995)). Amino acid sequences for the HIGN (residues 37 to 40 of SEQ ID NO: 3) and KISSS (residues 280 to 285 of SEQ ID NO: 3) motifs and flanking residues were aligned with CLUSTAL W (J. D. Thompson, D. G. Higgins, T. J. Gibson, *Nucleic Acids Res.* 22, 4673 (1994)) and all insertions and deletions then removed. A maximum parsimony tree was derived with the use of the programs SEQBOOT, PROTPARS, and CONSENSE from the PHYLIP 3.5c package (J. Felsenstein, Phylogeny Inference Package. Dept. Genet., Univ. Washington, Seattle (1993)). This gave rise to a phylogenetic tree with low replicate frequencies for more than 50% of the nodes.

21. A. R. Mushegian and E. V. Koonin, *Proc. Natl. Acad. Sci. U.S.A* 93, 10258 (1996).

22. R. A. Grayling, K. Sandman, J. N. Reeve, *FEMS Microbiol. Revs.* 18, 203 (1996); C. A. Ouzounis and N. C. Kyrpides, *J. Mol. Evol.* 42, 234 (1996).

23. A. Bergerat et al., *Nature* 386, 414 (1997).

24. Sequence alignment of motifs 1, 2, and 3 (18, 19) from class II LysRS enzymes against the most similar regions in euryarachaeal LysRS enzymes were determined. Class II and euryarchaeal sequences were separately aligned with CLUSTAL W and the aligned class II motifs (1, 2 or 3) used individually to search for similar regions in the euryarchaeal enzymes. The class II LysRS sequences from *Cricetulus longicaudatus* (GenBank accession number: Z31711), *Homo sapiens* (D31890), *Caenorhabditis elegans* (U41105), *Saccharomyces cerevisiae* cytoplasm (X56259), *Lycopersicon esculentum* (X94451), *E. coli* lysS (U28375), *E. coli* lysU (X16542), *Haemophilus influenzae* (P43825), *Acinetobacter calcoaceticus* (Z46863), *Bacillus subtilis* (P37477), *Staphylococcus aureus* (L36472), Synechocystis sp. (D90906), *Campylobacter jejuni* (M63448), *Thermus thermophilus* (P41255), *Mycoplasma genitalium* (P47382), *Mycoplasma pneumoniae* (AE000055), *Mycoplasma fermentans* (U50825), *Mycoplasma hominis* (P46191), *S. solfataricus* (Y08257) and *S. cerevisiae* mitochondria (X57360).

25. The sequence of the *M. maripaludis* lysS gene has been deposited in GenBank, accession no. AF009824.

26. Ibba, M., Morgan, S., Curnow, A. W., Pridmore, D. R., Vothknecht, U. C., Gardner, W., Lin, W., Woese, C. R., and Söll, D., *Science* 278, 1119 (1997).

27. Ibba, M., Bono, J. L., Rosa, P. A., and Söll, D., *Proc. Natl. Acad. Sci. USA* 94, 14383 (1997).

The papers cited in the above section and elsewhere in the application are expressly incorporated herein in their entireties by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The U.S. government has certain rights in the invention as it was made with partial support from N.I.G.M.S. grant number GM22854.

What is claimed is:

1. An isolated polypeptide comprising a lysyl-tRNA synthetase having at least about 85% sequence identity with SEQ ID NO: 3 or SEQ ID NO: 6.

2. A polypeptide according to claim 1 which bas at least about 90% sequence identity with SEQ ID NO: 3.

3. A polypeptide according to claim 2 which is SEQ ID NO: 3.

4. A polypeptide according to claim 1 which is a *Borrelia burgdorferi* class I-type lysyl tRNA synthetase.

5. A polypeptide according to claim 1 which has at least about 90% sequence identity with SEQ ID NO: 6.

6. A polypeptide according to claim 1 which is SEQ ID NO: 6.

7. A method for screening for inhibitors of *Borrelia burgdorferi* class I-type lysyl-tRNA synthetase enzyme inhibition using test molecules comprising (a) incubating a test molecule with an enzymatic polypeptide corresponding to SEQ ID NO: 3 in a mixture containing both lysine and tRNA for a time under conditions sufficient to observe acylation of the same tRNA with lysine in a control incubation of an enzymatic polypeptide corresponding to SEQ ID NO: 3 with lysine and the same tRNA under the same conditions, and (b) determining inhibition by observation of decreased acylation of the tRNA with lysine in the incubation with test molecule in comparison with a control.

8. A method according to claim 7 wherein the tRNA is naturally-occurring isolated *B. burgdorferi* tRNA.

9. A method according to claim 7 wherein the tRNA is synthetic tRNA encoded by SEQ ID NO: 12.

10. A method according to claim 7 wherein the tRNA is *E. coli* tRNA.

* * * * *